United States Patent
Criscione et al.

(10) Patent No.: US 9,833,318 B2
(45) Date of Patent: Dec. 5, 2017

(54) SELF-EXPANDING HEART ASSIST DEVICE

(71) Applicants: THE TEXAS A&M UNIVERSITY SYSTEM, College Station, TX (US); CorInnova Incorporated, Houston, TX (US)

(72) Inventors: John C. Criscione, College Station, TX (US); Christina M. Bolch, Houston, TX (US); Boris Leschinsky, Mahwah, NJ (US)

(73) Assignees: The Texas A&M University System, College Station, TX (US); Corinnova Incorporated, Houston, TX (US)

( * ) Notice: Subject to any disclaimer, the term of this patent is extended or adjusted under 35 U.S.C. 154(b) by 0 days.

(21) Appl. No.: 15/211,662

(22) Filed: Jul. 15, 2016

(65) Prior Publication Data

US 2017/0014233 A1    Jan. 19, 2017

Related U.S. Application Data

(60) Provisional application No. 62/192,725, filed on Jul. 15, 2015.

(51) Int. Cl.
  *A61F 2/24* (2006.01)
  *A61M 1/10* (2006.01)
  *A61M 1/12* (2006.01)

(52) U.S. Cl.
  CPC .......... *A61F 2/2481* (2013.01); *A61M 1/106* (2013.01); *A61M 1/1008* (2014.02); *A61F 2002/2484* (2013.01); *A61M 1/1068* (2013.01); *A61M 1/12* (2013.01)

(58) Field of Classification Search
  None
  See application file for complete search history.

(56) References Cited

U.S. PATENT DOCUMENTS

| | | |
|---|---|---|
| 2,826,193 A | 3/1958 | Vineberg |
| 3,034,501 A | 5/1962 | Hewson |
| 3,233,607 A | 2/1966 | Bolie |
| 3,513,836 A | 5/1970 | Sausse |
| 4,048,990 A | 9/1977 | Goetz |
| 4,185,617 A | 1/1980 | Hutchins |
| 4,536,893 A | 8/1985 | Parravicini |

(Continued)

FOREIGN PATENT DOCUMENTS

| | | |
|---|---|---|
| WO | 9922784 A1 | 5/1999 |
| WO | 0036995 A2 | 6/2000 |

(Continued)

OTHER PUBLICATIONS

Anstadt, et al., "Non-blood contacting biventricular support for severe heart failure." Ann Thorac Surg (2002), 73:556-62.

(Continued)

*Primary Examiner* — Brian T Gedeon
(74) *Attorney, Agent, or Firm* — Chainey P. Singleton

(57) ABSTRACT

The present invention includes a device and method for a self-expanding framework device adapted to facilitate the deployment of an extra-cardiac device. The device includes a deployment tube and a self-expanding wire framework having a structure that results in the self-expanding wire framework circumferential flaring motion and bending outwardly to advance around the heart.

23 Claims, 17 Drawing Sheets

(56) References Cited

U.S. PATENT DOCUMENTS

| | | |
|---|---|---|
| 4,685,446 A | 8/1987 | Choy |
| 5,089,017 A | 2/1992 | Young et al. |
| 5,119,804 A | 6/1992 | Anstadt |
| 5,131,905 A | 7/1992 | Grooters |
| 5,169,381 A | 12/1992 | Snyders |
| 5,256,132 A | 10/1993 | Snyders |
| 5,348,528 A | 9/1994 | Vince |
| 5,483,958 A | 1/1996 | Merberg et al. |
| 5,562,730 A | 10/1996 | Davidson |
| 5,627,630 A | 5/1997 | Matsumae et al. |
| 5,713,954 A | 2/1998 | Rosenberg et al. |
| 5,738,627 A | 4/1998 | Kovacs et al. |
| 5,749,839 A | 5/1998 | Kovacs |
| 5,863,574 A | 1/1999 | Julien |
| 6,155,968 A | 12/2000 | Wilk |
| 6,224,540 B1 | 5/2001 | Lederman et al. |
| 6,293,906 B1 | 9/2001 | Vanden Hoek et al. |
| 6,387,042 B1 | 5/2002 | Herrero |
| 6,540,666 B1 | 4/2003 | Chekanov |
| 6,592,619 B2 | 7/2003 | Melvin |
| 6,595,912 B2 | 7/2003 | Lau et al. |
| 6,602,182 B1 | 8/2003 | Milbocker |
| 6,602,184 B2 | 8/2003 | Lau et al. |
| 6,612,978 B2 | 9/2003 | Lau et al. |
| 6,612,979 B2 | 9/2003 | Lau et al. |
| 6,626,821 B1 | 9/2003 | Kung et al. |
| 6,663,558 B2 | 12/2003 | Lau et al. |
| 6,685,627 B2 | 2/2004 | Jayaraman |
| 6,723,039 B2 | 4/2004 | French et al. |
| 6,784,283 B2 | 8/2004 | Andersen et al. |
| 7,097,611 B2 | 8/2006 | Lau et al. |
| 7,229,405 B2 | 6/2007 | Lau et al. |
| 7,275,542 B2 | 10/2007 | Lurie et al. |
| 7,445,593 B2 | 11/2008 | Criscione |
| 7,489,380 B2 | 2/2009 | Lim et al. |
| 7,494,459 B2 | 2/2009 | Anstadt et al. |
| 7,674,222 B2 | 3/2010 | Nikolic et al. |
| 7,871,366 B2 | 1/2011 | Criscione et al. |
| 7,935,045 B2 | 5/2011 | Criscione et al. |
| 8,011,367 B2 | 9/2011 | Lurie et al. |
| 8,075,471 B2 | 12/2011 | Trumble |
| 8,187,160 B2 | 5/2012 | Criscione et al. |
| 8,192,351 B2 | 6/2012 | Fishler et al. |
| 8,550,976 B2 | 10/2013 | Criscione |
| 8,944,986 B2 | 2/2015 | Altman et al. |
| 9,259,520 B2 | 2/2016 | Altman et al. |
| 2002/0007216 A1 | 1/2002 | Melvin |
| 2002/0065449 A1 | 5/2002 | Wardle |
| 2003/0088151 A1 | 5/2003 | Kung et al. |
| 2004/0010180 A1 | 1/2004 | Scorvo |
| 2005/0004420 A1 | 1/2005 | Criscione |
| 2005/0187425 A1 | 8/2005 | Alferness et al. |
| 2005/0217677 A1 | 10/2005 | Lurie et al. |
| 2006/0241334 A1 | 10/2006 | Dubi et al. |
| 2006/0276683 A1 | 12/2006 | Feld et al. |
| 2006/0287568 A1 | 12/2006 | Jassawalla et al. |
| 2007/0015958 A1 | 1/2007 | Lau et al. |
| 2007/0016184 A1 | 1/2007 | Cropper et al. |
| 2007/0161846 A1 | 7/2007 | Nikolic et al. |
| 2007/0208214 A1 | 9/2007 | Hjelle et al. |
| 2007/0221222 A1 | 9/2007 | Lurie |
| 2007/0276444 A1 | 11/2007 | Galbart et al. |
| 2008/0004488 A1 | 1/2008 | Hjelle et al. |
| 2008/0021260 A1 | 1/2008 | Criscione et al. |
| 2008/0021266 A1 | 1/2008 | Laham et al. |
| 2008/0071134 A1 | 3/2008 | Dubi et al. |
| 2008/0257344 A1 | 10/2008 | Lurie et al. |
| 2009/0036730 A1 | 2/2009 | Criscione et al. |
| 2009/0043152 A1 | 2/2009 | Lau et al. |
| 2009/0062701 A1 | 3/2009 | Yannopoulos et al. |
| 2009/0118570 A1 | 5/2009 | Harrison et al. |
| 2009/0318746 A1 | 12/2009 | Thurmond, II et al. |
| 2010/0081867 A1 | 4/2010 | Fishler et al. |
| 2010/0152531 A1 | 6/2010 | Goodman et al. |
| 2010/0249519 A1 | 9/2010 | Park et al. |
| 2011/0021864 A1 | 1/2011 | Criscione et al. |
| 2011/0034776 A1 | 2/2011 | Dixon et al. |
| 2011/0040152 A1 | 2/2011 | Kim et al. |
| 2011/0166410 A1 | 7/2011 | Gutierrez et al. |
| 2013/0102849 A1* | 4/2013 | Criscione ............... A61B 1/32 600/204 |
| 2013/0150923 A1 | 6/2013 | Schnetz et al. |
| 2014/0194671 A1 | 7/2014 | Wildhirt |
| 2015/0165104 A1 | 6/2015 | Criscione et al. |

FOREIGN PATENT DOCUMENTS

| | | |
|---|---|---|
| WO | 03001971 A2 | 1/2003 |
| WO | 2004112867 A1 | 12/2004 |
| WO | 2006108177 A2 | 10/2006 |
| WO | 2007062239 A2 | 5/2007 |
| WO | 2008154033 A2 | 12/2008 |
| WO | 2009018358 A2 | 2/2009 |
| WO | 2011011641 A2 | 1/2011 |
| WO | 2011011642 A2 | 1/2011 |
| WO | 2012000003 A1 | 1/2012 |
| WO | 2012075460 A2 | 6/2012 |
| WO | 2012094064 A1 | 7/2012 |
| WO | 2013059316 A2 | 4/2013 |
| WO | 2014030140 A1 | 2/2014 |

OTHER PUBLICATIONS

Artrip, et al., "Physiological and hemodynamic evaluation of non-uniform direct cardiac compression." Circulation (1999), 100 (suppl II):236-43.

Cohn, et al. "Cardiac Remodeling—Concepts and Clinical Implications: A Consensus Paper From an International Forum on Cardiac Remodeling" Journal of the American College of Cardiology vol. 35, No. 3, Mar. 1, 2000.

Cooley, et al. "The past 50 years of cardiovascular surgery" (2000) Circulation 102: IV88-93.

Dipla, et al., "Myocyte Recovery After Mechanical Circulatory Support in Humans with End-stage Heart Failure." Circulation (1998), 97:2316-2322.

European Patent Office, Partial Supplementary European Search Report for EP 12841226.9 (PCT/US2012/060609), dated Jun. 9, 2015.

European Patent Office, European Search Report for EP 12841226.9 (PCT/US2012/060609), dated Dec. 14, 2015.

Feldman, et al. "Selective Changes in Cardiac Gene Expression During Compensated Hypertrophy and the Transition to Cardiac Decompensation in Rats with Chronic Aortic Banding" (Jul. 1993). Circ. Res. 73: 184-192.

Ghanta, et al, "Adjustable, Physiological Ventricular Restraint Improves Left Ventricular Mechanics and Reduces Dilation in an Ovine Model of Chronic Heart Failure," Mar. 13, 2007, Circuilation (10):Dec. 1, 2010.

Ghanta, et al, "Real-time Adjustment of Ventricular Restraint Therapy in Heart Failure," Dec. 2008, Eur. J. Cardiothorac Surg., 34(6):1136-40, available online Aug. 19, 2008.

Gheorhiad, et al. "Chronic heart failure in the united states: a manifestation of coronary artery disease" (1998) Circulation 97:282-9.

Goldstein, et al., "Medical progress: implantable left ventricular assist devices." N Engl J Med (Nov. 19, 1998), 339 (21):1522-1533.

Heerdt, et al., "Chronic Unloading by Left Ventricular Assist Device Reverses Contractile Dysfunction and Alters Gene Expression in End-Stage Heart Failure." Circulation (2000), 102:2713-2719.

Karvarana, et al., "Circulatory support with a direct cardiac compression device: a less invasive approach with the AbioBooster device." J Thorac Cardiovasc Surg, (Oct. 2001), 122:786-787.

Kawaguchi, et al., "Mechanical enhancement of myocardial oxygen saving by synchronized dynamic left ventricular compression." J Thorac Cardiovasc Surg (1992), 103:573-81 (Abstract Only).

Kherani, et al., "Ventricular Assist Devices as a Bridge to Transplant or Recovery." Cardiol (2004), 101:93-103.

(56) References Cited

OTHER PUBLICATIONS

Machine Translation of WO 2012/000003 (PCT/AT2011/000218)—Publication date Jan. 5, 2012—Abstract, description & claims, 21 pp.

Mann, et al, "Mechanisms and Models in Heart Failure: the Biomechanical Model and Beyond," May 31, 2005, Circulation, 111(21):2837-49.

Mann, et al, "Left Ventricular Size and Shape: Determinants of Mechanical Signal Transduction Pathways," 2005, Heart Failure Reviews, vol. 10, No. 2, pp. 95-100.

Moreno, et al, "Assessment of Minimally Invasive Device That Provides Simultaneous Adjustable Cardiac Support and Active Synchronous Assist in an Acute Heart Failure Model," Journal of Medical Devices, Dec. 2011, vol. 5 / 041008-1.

Omens, J.H. "Stress and strain as regulators of myocardial growth." Prog. Biophys. Molec. Biol. (1998), 69:559-572.

Oz, et al., "Direct Cardiac Compression Devices." J Heart Lung Transplant (Oct. 2002), 21:1049-1055.

Rose, et al., "Long-Term Use of Left Ventricular Assist Device for End-stage Heart Failure." N Engl J Med (Nov. 15, 2001), 345(20):1435-1443.

Snowden, et al. "Modulation of Diastolic Filling Using an Epicardial Diastolic Recoil Device" Journal of Medical Devices Sep. 2013, vol. 7 / 034503-1.

Tamminen, et al., "Ectopic Expression of AB13 Gene Enhances Freezing Tolerance in Response to Abscisic Acid and Low Temperature in Arabidopsis Thaliana," The Plant Journal, (2001), 25(1):1-8.

Williams, et al. "Direct cardiac compression for cardiogenic shock with the CardioSupport System." Ann Thorac Surg (2001), 71:S188-9.

United States Patent & Trademark Office (ISA), International Search Report and Written Opinion for PCT/US2005/003343 dated Jul. 16, 2007.

European Patent Office, Supplementary European Search Report for EP 10802924.0 (PCT/US2010/042970), dated Sep. 27, 2012.

European Patent Office (ISA), Written Opinion for PCT/US2004/019809 dated Oct. 24, 2005—8 pp.

Korean Intellectual Property Office (ISA), International Search Report for PCT/US2010/042970, dated May 2, 2011, 13 pp.

Korean Intellectual Property Office (ISA), International Search Report and Written Opinion for PCT/US2010/042972, dated Apr. 14, 2011, 8 pp.

Korean Intellectual Property Office (ISA), International Search Report for PCT/US2008/071618 dated Feb. 12, 2009.

Korean Intellectual Property Office (ISA), International Search Report and Written Opinion for PCT/US2011/063178 dated Jun. 25, 2012—14 pp.

Korean Intellectual Property Office (ISA), International Search Report and Written Opinion for PCT/US2012/060609 dated Apr. 19, 2013—15 pp.

United States Patent & Trademark Office (ISA) (Corrected), International Search Report and Written Opinion for PCT/US2006/013457 dated Dec. 10, 2007.

United States Patent & Trademark Office (ISA), International Search Report and Written Opinion for PCT/US2016/029756 dated Jul. 27, 2016.

United States Patent & Trademark Office (ISA), International Search Report and Written Opinion for PCT/US2016/042578 dated Oct. 19, 2016.

\* cited by examiner

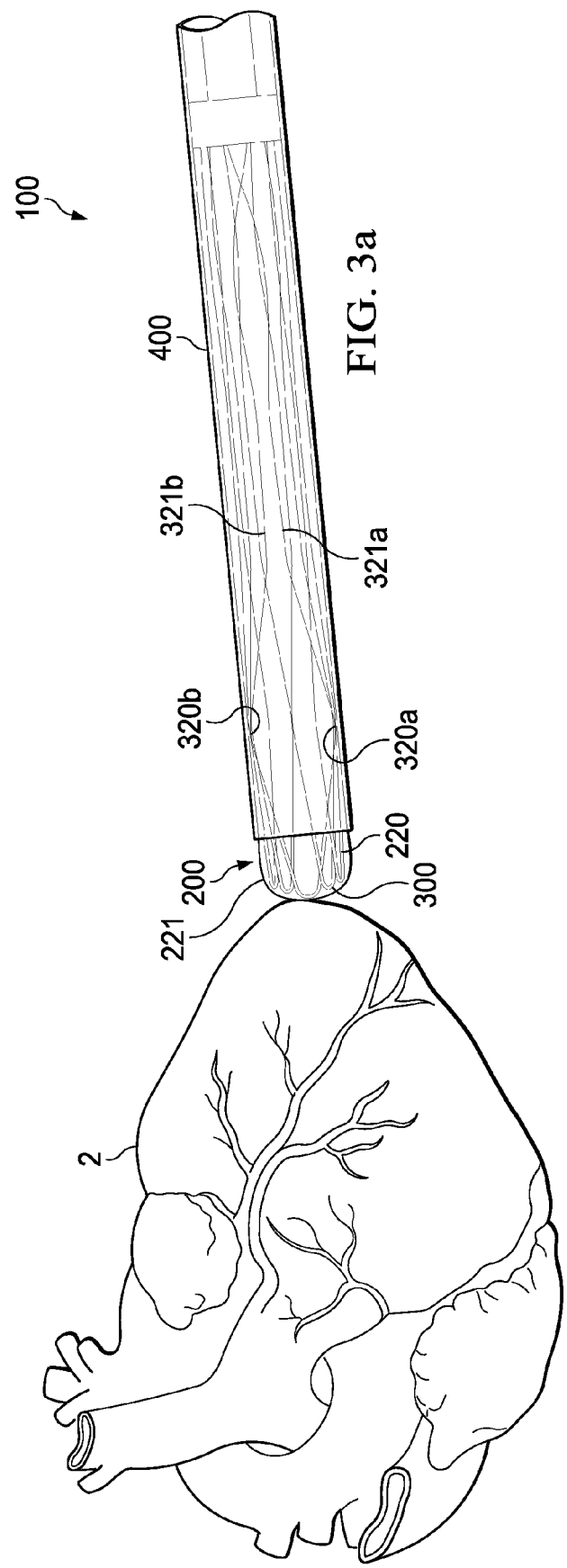

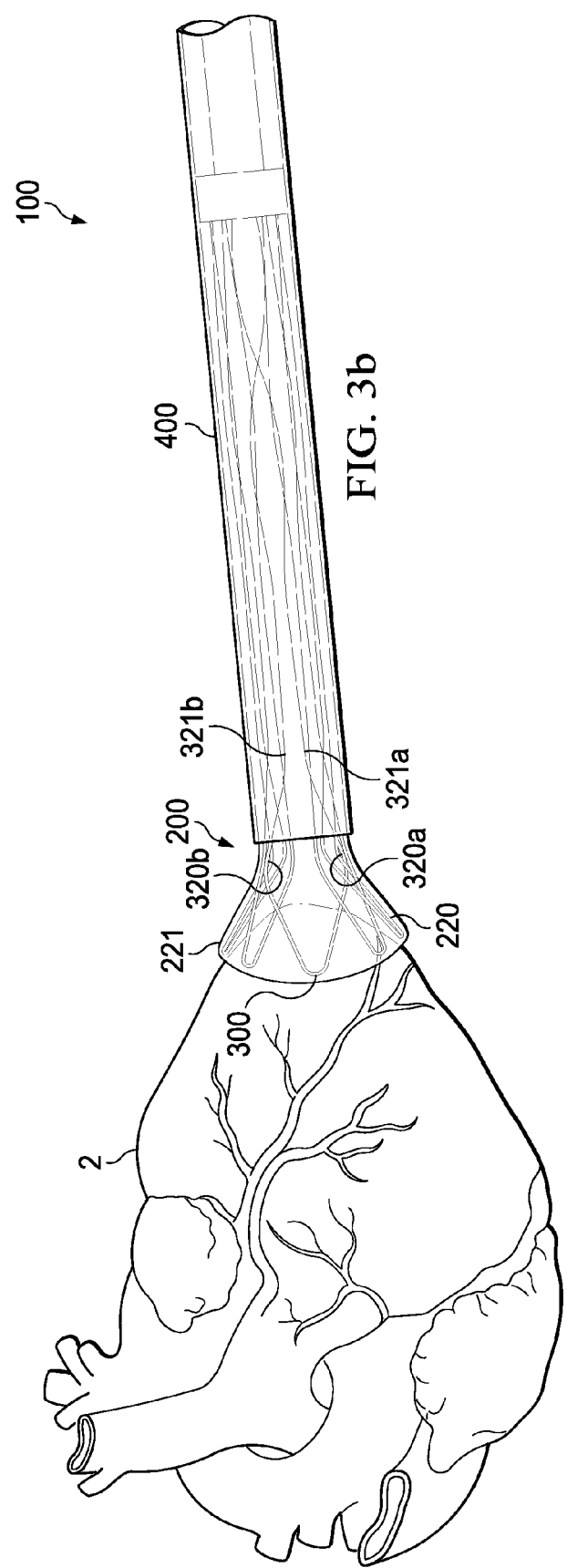

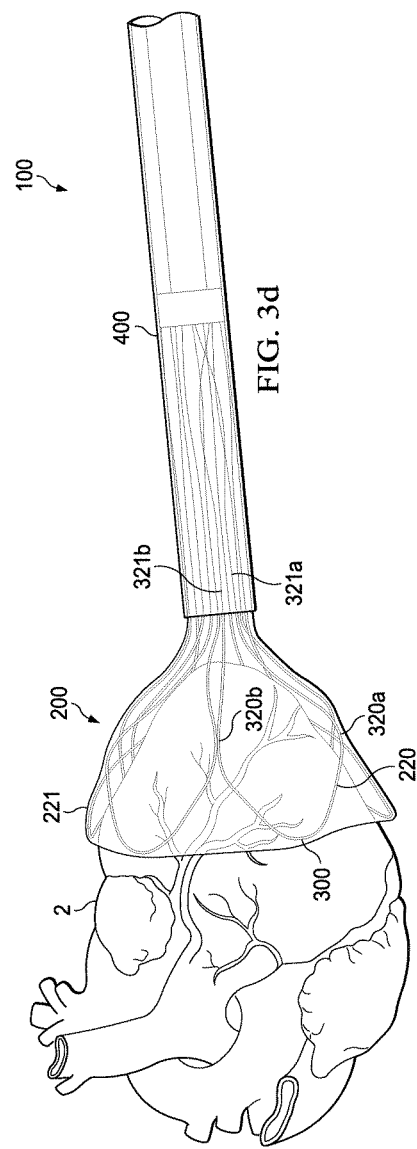

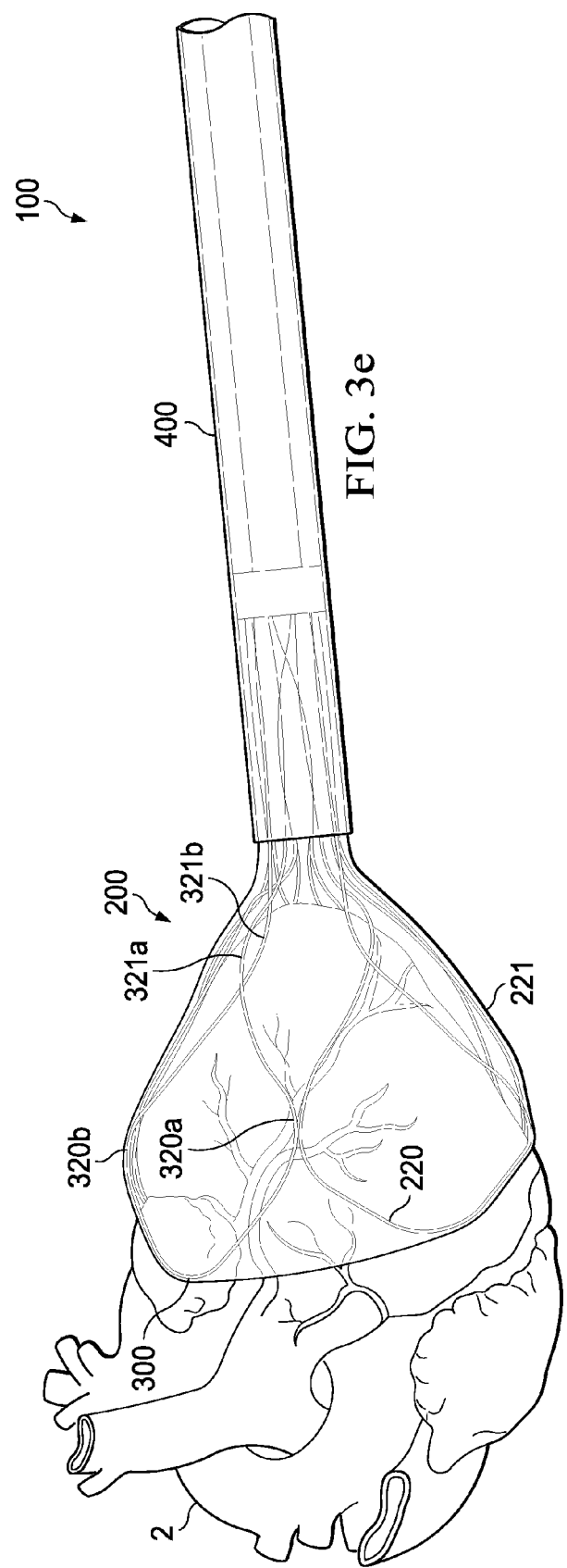

SELF-EXPANDING HEART ASSIST DEVICE

CROSS-REFERENCE TO RELATED APPLICATIONS

This application claims priority to U.S. Provisional Application Ser. No. 62/192,725 filed Jul. 15, 2015, the entire contents of which is incorporated herein by reference.

TECHNICAL FIELD OF THE INVENTION

The present invention relates in general to the field of heart assist devices, and more particularly, to a method and device for minimally invasive delivery of extra-cardiac devices.

STATEMENT OF FEDERALLY FUNDED RESEARCH

Not applicable.

INCORPORATION-BY-REFERENCE OF MATERIALS FILED ON COMPACT DISC

Not applicable.

BACKGROUND OF THE INVENTION

Without limiting the scope of the invention, its background is described in connection with methods and devices for delivery or deployment of minimally invasive extra-cardiac devices. One treatment for patients who suffer from either a myocardial infarction or CHF is the implantation of a direct cardiac compression device. Currently, a sternotomy is the preferred method of implantation of the cardiac compression device. Sternotomy is a type of surgical procedure in which a vertical inline incision is made along the sternum, after which the sternum itself is divided, or "cracked". This procedure provides access to the heart for surgical procedures. Conventional direct cardiac compression devices, such as the Anstadt cup, require a sternotomy for implantation, which is a very painful procedure. Disadvantageously, sternotomies result in long recovery times and a high risk of infection. Further, there is a high risk of complications due to the lengthy surgery required for these unstable patients.

Current approaches to minimally invasive implantation of heart-assist devices of various types suffer the shortcoming of being relatively slow and difficult procedures, resulting in additional stress on the patient and reducing the likelihood of a favorable outcome. Current minimally invasive devices may be deployed via a system of guidewires placed between the pericardium and the heart. There is a need to insert minimally invasive assistive biotechnology apparatuses such as a direct cardiac compression device (DCCD) in a minimally invasive way without the use of guidewires.

SUMMARY OF THE INVENTION

The present inventors recognized a need for minimally invasive devices to be deployed without the help of guidewires. In addition to speeding up insertion procedure, the present invention reduces the risk of guidewire entanglement to the patient.

The present invention provides a self-expanding wire framework comprising: a self-expanding wire framework covered with a polymer film adapted to flare outwardly to encircle a portion of the heart, wherein the self-expanding wire framework comprises: a set of articulated wire loops extending from a lead edge to a hub, wherein each of the articulated wire loops of the set of articulated wire loops comprise a top segment positioned at the lead edge and that extends to a left midway bend and to a right midway bend, a left strut that extends from the left midway bend to the hub, a right strut that extends from the right midway bend to the hub, and a fixed strut attachment point on the hub to fix the position of the left strut and the right strut, wherein the left midway bend and right midway bend result in a tension that causes the self-expanding wire framework and the polymer film to engage in a circumferential flaring motion and bend outwardly as the self-expanding framework is deployed from the deployment tube. The left midway bends and the right midway bends may be rounded to allow for gradual flaring as the self-expanding wire framework is deployed. The left midway bends and the right midway bends may be flattened to allow for flaring as the self-expanding wire framework is deployed. The left midway bends and the right midway bends may further comprise multiple bends to allow for immediate flaring positions as the self-expanding wire framework is deployed. The articulated wire loops may be a non-rounded wire. The set of articulated wire loops may comprises at least 2, 3, 4, 5, 6, 7, 8, 9, 10, 11, 12, 13, 14, 15, 16, 17, 18, 19, 20 or more articulated wire loops. The left strut may be connected to the right strut between the midway bend and the hub. The left strut may be intertwined with the right strut between the midway bend and the hub. The left strut and the right strut may be connected separately at the hub. Each of the articulated wire loops of the set of articulated wire loops may be positioned adjacent to an adjacent articulated wire loop. Each of the articulated wire loops of the set of articulated wire loops may be positioned to at least partially overlap the adjacent articulated wire loop. The polymer film may be on the inside of the self-expanding wire framework. The polymer film may be on the outside of the self-expanding wire framework. The polymer film may be on the inside and the outside to sandwich the self-expanding wire framework. The left strut and the right strut each may comprise a bend end connected to the midway bend and a hub end, wherein the hub end is secured to the hub at a fixed strut attachment point. The device may further comprising a deployment tube having an outer surface surrounding an inner passage and a deployment aperture at one end of the inner passage, wherein the self-expanding wire framework covered with a polymer film is slidably positioned in the inner passage to slidably extend from the deployment aperture and adapted to flare outwardly to encircle a larger portion of the heart. The self-expanding wire framework may be positioned inside the deployment tube and the top segments are bent, and the left midway bends and the right midway bends are straightened.

The present invention provides a self-expanding framework device adapted to facilitate the deployment of an extra-cardiac device, comprising: a deployment tube having an outer surface surrounding an inner passage and a deployment aperture at one end of the inner passage, and a self-expanding wire framework covered with a polymer film and slidably positioned in the inner passage to slidably extend from the deployment aperture and adapted to flare outwardly to encircle a larger portion of the heart, wherein the self-expanding wire framework comprises: a set of articulated wire loops extending from a lead edge to a hub, wherein each of the articulated wire loops of the set of articulated wire loops comprise a top segment positioned at the lead edge and that extends to a left midway bend and to a right midway bend, a left strut that extends from the left midway bend to the hub, a right strut that extends from the right midway bend to the hub, and a fixed strut attachment point on the hub to fix the position of the left strut and the right strut, wherein the left midway bend and right midway bend result in a tension that causes the self-expanding wire framework and the polymer film to engage in a circumferential flaring motion and bend outwardly as the self-expanding framework is deployed from the deployment tube.

The self-expanding wire framework is positioned inside the deployment tube with the top segments bent such that the left midway bends and the right midway bends are relatively straightened. The left midway bends and the right midway bends are rounded to allow for gradual flaring as the self-expanding wire framework is deployed from the deployment tube. The left midway bends and the right midway bends are flattened to allow for flaring as the self-expanding wire framework is deployed from the deployment tube. The left midway bends and the right midway bends further comprise multiple bends to allow for immediate flaring positions as the self-expanding wire framework is deployed from the deployment tube. The articulated wire loops may be a non-rounded wire. The set of articulated wire loops may comprises at least 2, 3, 4, 5, 6, 7, 8, 9, 10, 11, 12, 13, 14, 15, 16, 17, 18, 19, 20 or more articulated wire loops. The left strut may be connected to the right strut between the midway bend and the hub. The left strut may be intertwined with the right strut between the midway bend and the hub. The left strut and the right strut may be connected separately at the hub. Each of the articulated wire loops of the set of articulated wire loops may be positioned adjacent to an adjacent articulated wire loop. Each of the articulated wire loops of the set of articulated wire loops may be positioned to at least partially overlap the adjacent articulated wire loop. The polymer film may be on the inside of the self-expanding wire framework. The polymer film may be on the outside of the self-expanding wire framework. The polymer film may be on the inside and the outside to sandwich the self-expanding wire framework. The left strut and the right strut each may comprise a bend end connected to the midway bend and a hub end, wherein the hub end is secured to the hub at a fixed strut attachment point. The device may further comprising a deployment tube having an outer surface surrounding an inner passage and a deployment aperture at one end of the inner passage, wherein the self-expanding wire framework covered with a polymer film is slidably positioned in the inner passage to slidably extend from the deployment aperture and adapted to flare outwardly to encircle a larger portion of the heart. The self-expanding wire framework may be positioned inside the deployment tube and the top segments are bent, and the left midway bends and the right midway bends are straightened.

The present invention provides a method for implanting an extra-cardiac device about the heart using a self-expanding framework delivery device about a heart, comprising the steps of: providing a self-expanding framework delivery device comprising a deployment tube having an outer surface surrounding an inner passage and a deployment aperture at one end of the inner passage, and a self-expanding wire framework covered with a polymer film and slidably positioned in the inner passage to slidably extend from the deployment aperture and adapted to flare outwardly to encircle a larger portion of the heart, wherein the self-expanding wire framework comprises: a set of articulated wire loops extending from a lead edge to a hub, wherein each of the articulated wire loops of the set of articulated wire loops comprise a top segment positioned at the lead edge and that extends to a left midway bend and to a right midway bend, a left strut that extends from the left midway bend to the hub, a right strut that extends from the right midway bend to the hub, and a fixed strut attachment point on the hub to fix the position of the left strut and the right strut, wherein the left midway bend and right midway bend result in a tension that causes the self-expanding wire framework and the polymer film to engage in a circumferential flaring motion and bend outwardly as the self-expanding framework is deployed from the deployment tube; inserting the deployment tube into the thoracic cavity; deploying the self-expanding wire framework covered with a polymer film from the deployment aperture; bending outwardly of the self-expanding framework at the left midway bend and right midway to circumferential flare the lead edge of the articulated wire loops about the apex of the heart; and extending the self-expanding wire framework from the deployment aperture to encircle a portion of the heart. The left midway bends and the right midway bends may be rounded to allow for gradual flaring as the self-expanding wire framework is deployed. The left midway bends and the right midway bends may be flattened to allow for flaring as the self-expanding wire framework is deployed. The left midway bends and the right midway bends may further comprise multiple bends to allow for immediate flaring positions as the self-expanding wire framework is deployed. The articulated wire loops may be a non-rounded wire. The set of articulated wire loops may comprises at least 2, 3, 4, 5, 6, 7, 8, 9, 10, 11, 12, 13, 14, 15, 16, 17, 18, 19, 20 or more articulated wire loops. The left strut may be connected to the right strut between the midway bend and the hub. The left strut may be intertwined with the right strut between the midway bend and the hub. The left strut and the right strut may be connected separately at the hub. Each of the articulated wire loops of the set of articulated wire loops may be positioned adjacent to an adjacent articulated wire loop. Each of the articulated wire loops of the set of articulated wire loops may be positioned to at least partially overlap the adjacent articulated wire loop. The polymer film may be on the inside of the self-expanding wire framework. The polymer film may be on the outside of the self-expanding wire framework. The polymer film may be on the inside and the outside to sandwich the self-expanding wire framework. The left strut and the right strut each may comprise a bend end connected to the midway bend and a hub end, wherein the hub end is secured to the hub at a fixed strut attachment point. The device may further comprise a deployment tube having an outer surface surrounding an inner passage and a deployment aperture at one end of the inner passage, wherein the self-expanding wire framework covered with a polymer film is slidably positioned in the inner passage to slidably extend from the deployment aperture and adapted to flare outwardly to encircle a larger portion of the heart. The self-expanding wire framework may be positioned inside the deployment tube and the top segments are bent, and the left midway bends and the right midway bends are straightened.

The present invention provides a self-expanding wire framework comprising: a self-expanding wire framework covered with a polymer film. The polymer film may be a passive covering for the purposes of a passive device for diastolic heart failure. The passive covering may include one or more fluid chambers that are passively filled with fluid to compress the heart. The passive covering may include a port to adjust the volume of fluid in the passive chambers as desired.

In another embodiment the polymer film may include active inflation chambers to assist the heart. The device comprising a polymer film adapted to fit about the heart, wherein the polymer film is in contact with the heart; an outer film in contact with the biocompatible inner film; one or more fluid chambers formed between the biocompatible inner film and the outer film; and a fluid connection in fluid communication with the one or more fluid chambers, wherein a fluid enters the one or more fluid chambers through the fluid connection to selectively compress the heart during a heart contraction and during recoil the fluid exits the one or more fluid chambers through the fluid connection to allow the heart to decompress. The device may further comprise a pneumatic driver operably linked to the fluid connection to pressurize the biocompatible inner membrane to compress the heart and depressurize the biocompatible inner membrane to aid in filling the heart. In another embodiment the polymer film comprises a biocompatible inner film pneumatically locked to the heart to allow the inner film to pull open the heart and aid in filling of the heart.

In another embodiment the polymer film may include both an active set of chambers and a passive set of chambers. The device comprising an inner polymer film comprising one or more passive chambers adapted to fit about the heart. Each of the one or more passive chambers may be individually filled with a fixed volume of fluid. This fixed volume of fluid may be varied through a port to change the size of the one or more passive chambers and thus the fitment of the device about the heart. The device also includes an outer film in contact with the inner film; one or more fluid chambers formed between the inner film and the outer film; and a fluid connection in fluid communication with the one or more fluid chambers, wherein a fluid enters the one or more fluid chambers through the fluid connection to selectively compress the heart during a heart contraction and during recoil the fluid exits the one or more fluid chambers through the fluid connection to allow the heart to decompress. The device may further comprise a pneumatic driver operably linked to the fluid connection to pressurize the biocompatible inner membrane to compress the heart and depressurize the biocompatible inner membrane to aid in filling the heart. In another embodiment the polymer film comprises a biocompatible inner film pneumatically locked to the heart to allow the inner film to expand the heart and aid in filling of the heart.

The present invention provides a self-expanding wire framework comprising: a self-expanding wire framework covered with a polymer film adapted to flare outwardly to encircle a portion of the heart, wherein the self-expanding wire framework comprises: a set of articulated wire loops extending from a lead edge to a hub, wherein each of the articulated wire loops of the set of articulated wire loops comprise a top segment positioned at the lead edge and that extends to a left midway bend and to a right midway bend, a left strut that extends from the left midway bend to the hub, a right strut that extends from the right midway bend to the hub, and a fixed strut attachment point on the hub to fix the position of the left strut and the right strut, wherein the left midway bend and right midway bend result in a tension that causes the self-expanding wire framework and the polymer film to engage in a circumferential flaring motion and bend outwardly as the self-expanding framework is deployed from the deployment tube. The left midway bends and the right midway bends may be rounded to allow for gradual flaring as the self-expanding wire framework is deployed. The left midway bends and the right midway bends may be flattened to allow for flaring as the self-expanding wire framework is deployed. The left midway bends and the right midway bends may further comprise multiple bends to allow for immediate flaring positions as the self-expanding wire framework is deployed. The articulated wire loops may be a non-rounded wire. The set of articulated wire loops may comprises at least 2, 3, 4, 5, 6, 7, 8, 9, 10, 11, 12, 13, 14, 15, 16, 17, 18, 19, 20 or more articulated wire loops. The left strut may be connected to the right strut between the midway bend and the hub. The left strut may be intertwined with the right strut between the midway bend and the hub. The left strut and the right strut may be connected separately at the hub. Each of the articulated wire loops of the set of articulated wire loops may be positioned adjacent to an adjacent articulated wire loop. Each of the articulated wire loops of the set of articulated wire loops may be positioned to at least partially overlap the adjacent articulated wire loop. The polymer film may be on the inside of the self-expanding wire framework. The polymer film may be on the outside of the self-expanding wire framework. The polymer film may be on the inside and the outside to sandwich the self-expanding wire framework. The left strut and the right strut each may comprise a bend end connected to the midway bend and a hub end, wherein the hub end is secured to the hub at a fixed strut attachment point. The device may further comprising a deployment tube having an outer surface surrounding an inner passage and a deployment aperture at one end of the inner passage, wherein the self-expanding wire framework covered with a polymer film is slidably positioned in the inner passage to slidably extend from the deployment aperture and adapted to flare outwardly to encircle a larger portion of the heart. The self-expanding wire framework may be positioned inside the deployment tube and the top segments are bent, and the left midway bends and the right midway bends are straightened.

BRIEF DESCRIPTION OF THE DRAWINGS

For a more complete understanding of the features and advantages of the present invention, reference is now made to the detailed description of the invention along with the accompanying figures and in which:

FIGS. 3a-3e depicts the present invention at successive amounts of deployment about a plastic mock heart.

DETAILED DESCRIPTION OF THE INVENTION

Figure 1:
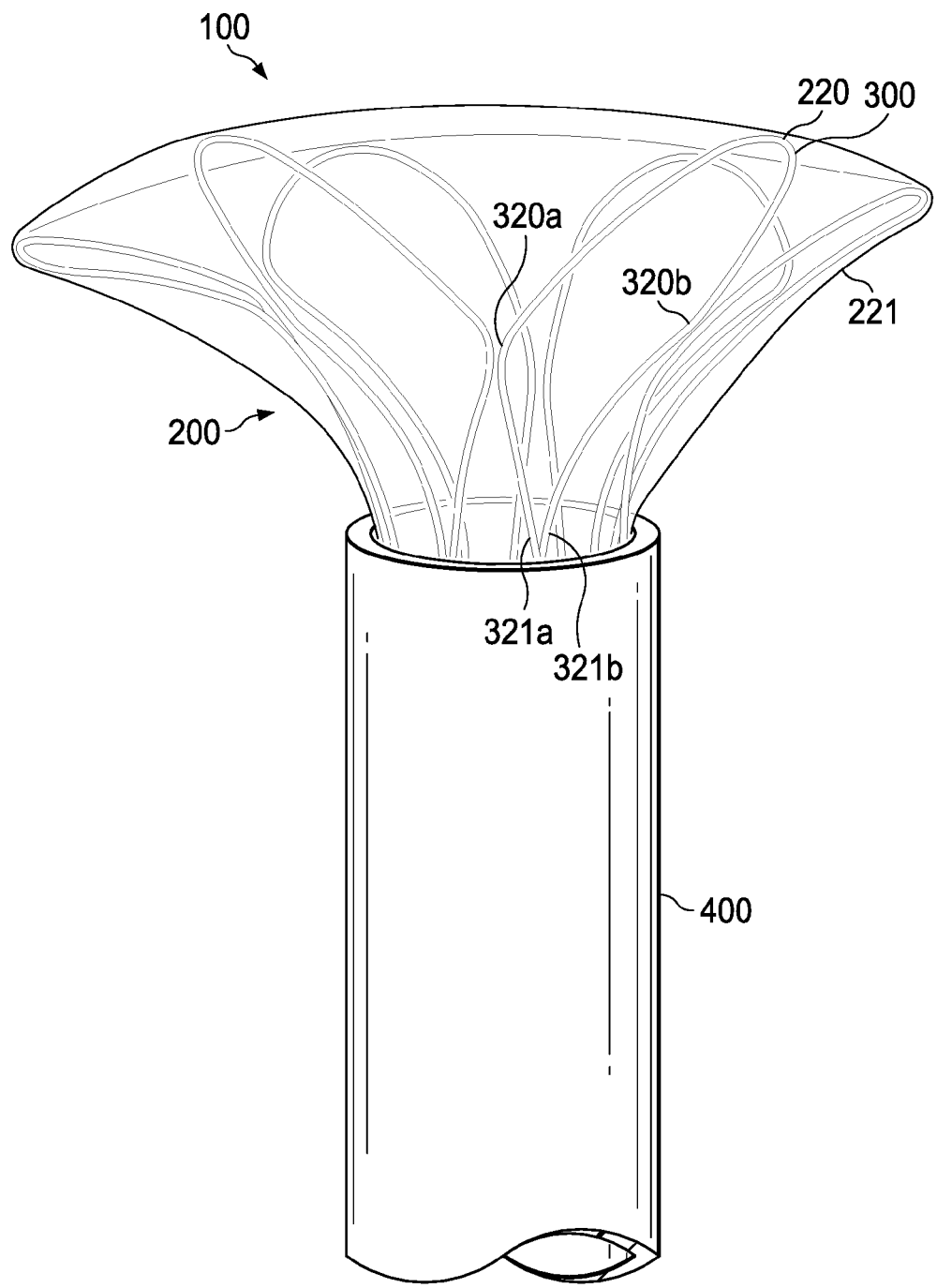
FIG. 1 depicts a frontal view of an embodiment of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Though different devices exist today with specific indications for medium/long term support, devices that provide direct cardiac compression and aortic compression represent a significant innovation in the cardiac device industry as it can address both systolic and diastolic heart failure with a single device design.

The present invention is directed to a minimally invasive implantation apparatus and method and is adapted to save the lives of CHF patients and dramatically shorten their hospital stays. With the present invention, in combination with drug therapy and an exercise program, many of the patients receiving a deployed device, such as a cardiac compression device, in accordance with the present invention, could have restored cardiac function in as little as three weeks, allowing a shorter hospital stay and increased quality of life.

As noted, direct cardiac compression devices require a sternotomy for implantation. In contrast, the present invention permits at least a deployable device to be implanted quickly using a minimally invasive incision without the need for any assisting devices or guidewires. This allows patients to recover within a shorter period, resulting in a shorter hospital stays and less of a chance for infection.

As used herein the term "polymer" or 'polymer film" is use to denote a polymeric composition that is biocompatible. Non-limiting examples of suitable, biocompatible, biostable, implantable materials include but are not limited to polyetherurethane, polycarbonateurethane, silicone, polysiloxaneurethane, hydrogenated polystyrene-butadiene copolymer, ethylene-propylene and dicyclopentadiene terpolymer, and/or hydrogenated poly(styrene-butadiene) copolymer, poly(tetramethylene-ether glycol) urethanes, poly(hexamethylenecarbonate-ethylenecarbonate glycol) urethanes elastomeric polyurethane, latex, polyetherurethane, polycarbonateurethane, silicone, polysiloxaneurethane, hydrogenated polystyrene-butadiene copolymer, ethylene-propylene and dicyclopentadiene terpolymer, hydrogenated poly(styrene-butadiene) copolymer, poly(tetramethylene-ether glycol) urethanes, poly(hexamethylenecarbonate-ethylenecarbonate glycol) urethanes and combinations thereof. In addition, the present invention may be reinforced with filaments, made of a biocompatible, biostable, implantable polyamide, polyimide, polyester, polypropylene, polyurethane etc. In addition, the device may be made from different materials in different regions of the device.

The present invention can be broadly viewed as a device comprising a deployment tube having an inner surface and an outer surface, and a self-expanding wire framework slidable along the inner surface. As shown in FIG. 1, embodiment 100 of the present invention comprises a deployment tube 400 with the self-expanding wire framework 200 having polymer film 221 and being partially deployed from the deployment tube 400. In one embodiment, the DCCD device (not shown) can be attached to the self-expanding wire framework 100 before being drawn into the deployment tube 400.

FIG. 1 shows the device 100 having a framework 200 with the polymer film 221 in contact six articulated wire loops 220 being deployed from tube 400. The leading edge or top segments 300 forms a framework 200 encloses the deployed device 100 around the heart (not shown). The self-expanding wire framework 200 comprises multiple articulated wire loops 220 adjacent each other but not intertwined and disposed in a polymer film 221. Each of the articulated wire loops 220 includes the midway bends 320*a* and 320*b* to create tension when the midway bends 320*a* and 320*b* rotate and straighten. The articulated wire loops 220 include strut 321*a* extending from midway bends 320*a* and strut 321*b* extending from midway bends 320*b*. In FIG. 1, the top segment 300 is pointed outwards or flaring, by doing so, the left and right midway bends 320*a* and 320*b*. When the top segment 300 is further deployed axially, the left and right midway bends 320*a* and 320*b* must become straighter or unbend forming a configuration with higher elastic energy. As left and right midway bends 320*a* and 320*b* of each further rotate and straighten out, this will orient the top segment 300 to straighten out from the initial flaring motion when the framework is first deployed.

Figure 2A:
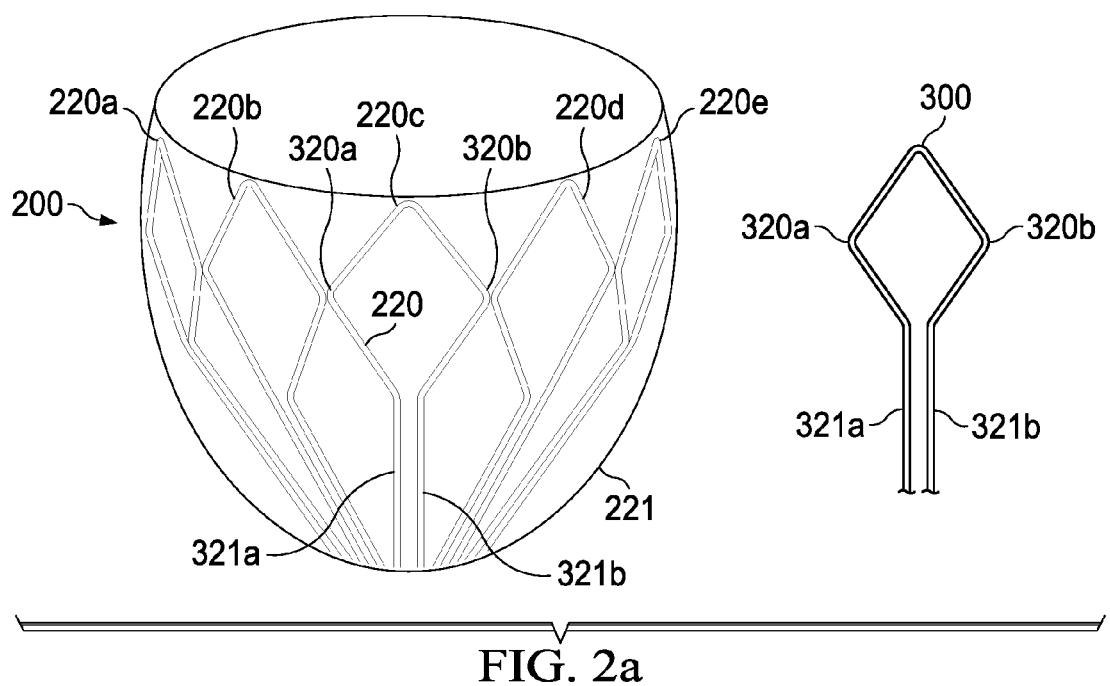
FIGS. 2a and 2b depict a schematic diagram of the elements of the self-expanding wire framework.
Figure 2B:
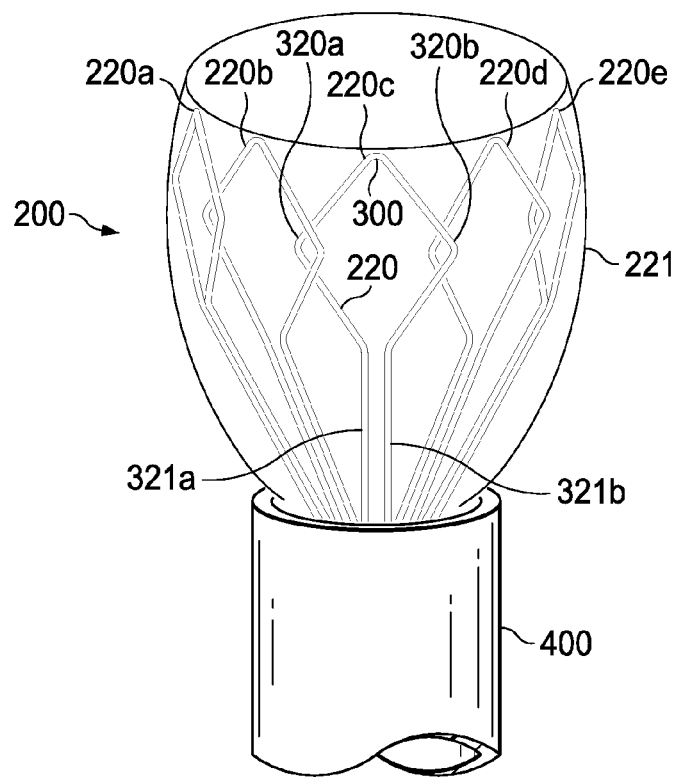

FIGS. 2*a* and 2*b* depict a schematic diagram of the elements of self-expanding wire framework 200 with a polymer film 221 covering. The self-expanding wire framework 200 is comprised of multiple articulate wire loops 220*a-e*, each comprising of a left and a right midway bends 320*a* and 320*b* that extend as struts 321*a* and 321*b* to hub (not shown). When the self-expanding wire framework 200 is being drawn into or compressed to fit inside the deployment tube (not shown), the top segment 300 of each articulated loops 220 is bent and compressed together to fit inside the deployment tube (not shown). The midway bends 320*a* and 320*b* of each articulated loop are straightened and compressed closer together to one another. The unbending or straightening of midway bends 320*a* and 320*b* is unstable causing it to twist or rotate rather than becoming a straight line (when struts 321*a* and 321*b* are not fixed relative to each other). When the left and right midway bends 320*a* and 320*b* of each articulated loop 220 are compressed closer together, the left and right midway bends 320*a* and 320*b* rotate and orient the top segment 300 out-of-plane creating a flaring motion. The unstable tendency of unbending makes the top segment 300 of each articulate loop 220 protrudes radially outwards away from the hoop dimension as the top segment 300 is partially deployed.

FIG. 2*a* shows a schematic diagram and the overall shape of the self-expanding wire framework 200 having adjacent articulated wire loops 220*a-e* and polymer film 221 fully deployed from the deployment tube (not shown). The leading edge or top segment 300 forms a circular framework 200 that encloses the deployed device around the heart (not shown). The self-expanding wire frame 200 comprises multiple articulated wire loops 220*a-e* disposed in a polymer film 221. The articulated wire loops 220*a-e* are adjacent each other but not intertwined. The polymer film 221 may be on one side (inner surface or outer surface) of the multiple articulated wire loops 220. The polymer film 221 may be on both sides (inner surface and outer surface) of the multiple articulated wire loops 220*a-e* forming a sandwich configuration. Alternatively, the polymer film 221 may be a single film with the multiple articulated wire loops 220a-e disposed within the polymer film 221. Each of the articulated wire loops 220a-e includes the midway bends 320a and 320b as shown in the diagram to create tension when the midway bends 320a and 320b rotate and straighten. The articulated wire loops 220a-e include strut 321a extending from midway bends 320a and strut 321b extending from midway bends 320b. The position of strut 321a and 321b are fixed relative each other so that the strut 321a and 321b themselves cannot rotate or turn thus forcing movement about the midway bends 320a and 320b. The left midway bend 320a and right midway bend 320b of each of the articulated wire loops 220a-e results in a tension that causes the self-expanding wire framework 200 to engage in a circumferential flaring motion and end out of plane when deployed from the deployment tube (not shown). Further deployment of the framework 200 allows the left and right midway bends 320a and 320b of each of the articulated wire loops 220a-e making up the framework 200 to straighten out in a configuration with higher elastic energy which reorients the top segment 300 back towards the center.

FIG. 2b shows a schematic diagram and the overall shape of the self-expanding wire framework 200 having overlapping articulated wire loops 220 with the polymer film 221 covering that is fully deployed from the deployment tube (not shown). The leading edge or top segment 300 forms a circular framework 200 that encloses the deployed device around the heart (not shown). The self-expanding wire framework 200 comprises multiple articulated wire loops 220 disposed in a polymer film 221 in a partially overlapping pattern with the adjacent wire loops 220 partially overlapping (but not intertwined). The polymer film 221 may be on one side (inner surface or outer surface) of the multiple articulated wire loops 220. The polymer film 221 may be on both sides (inner surface and outer surface) of the multiple articulated wire loops 220 forming a sandwich configuration. Alternatively, the polymer film 221 may be a single film with the multiple articulated wire loops 220 disposed with in the polymer film 221. Each of the articulated wire loops 220 includes the midway bends 320a and 320b as shown in the diagram to create tension when the midway bends 320a and 320b rotate and straighten. The articulated wire loops include strut 321a extending from midway bends 320a and strut 321b extending from midway bends 320b. The position of strut 321a and 321b are fixed relative to each other so that the strut 321a and 321b cannot rotate or turn forcing movement about the midway bends 320a and 320b. The left midway bend 320a and right midway bend 320b of each of the articulated wire loops 220 results in a tension that causes the self-expanding wire framework 200 to engage in a circumferential flaring motion and end out of plane when deployed from the deployment tube. Further deployment of the framework 200 allows the left and right midway bends 320a and 320b of each of the articulated wire loops 220 making up the framework 200 to straighten out in a configuration with higher elastic energy which reorients the top segment 300 back towards the center. The self-expanding wire framework 200 has partially overlapping articulated wire loops 220 which are covered by polymer film 221. Each articulated wire loop has a left midway bend 320a and a right midway bend 320b. The adjacent wire loop at least partially overlaps a second wire loop by placing the left midway bend of a first wire loop behind the right midway bend of the second wire loop this pattern is repeated until the desired number of the articulated wire loops are achieved.

To illustrate how the self-expanding wire framework 200 able to advance around a heart 2 from an apical approach, FIGS. 3a-3b depict an embodiment of the present invention at successive amounts of deployment about a plastic mock heart 2 (3D printed from a CT scan of a normal adult sheep).

FIGS. 3a-3e illustrated the flaring and straightening of the framework 200 as it was deployed from the deployment tube 400. However, the flaring motion can also be observed with just a single articulated wire loop as seen in FIGS. 4-8.

FIG. 3a shows the self-expanding wire framework 200 compressed inside deployment tube 400 as it is deployed about a plastic mock heart 2. FIG. 3a shows a polymer film 221 with an articulated wire loop 220 with the top segment 300 flanked by the left and right midway bends 320a and 320b and include strut 321a extending from midway bends 320a and strut 321b extending from midway bends 320b as it is deployed from the deployment tube 400. The articulated wire loop 220 is deployed from the deployment tube 400 such that the left and right midway bends 320a and 320b are within the deployment tube 400.

FIG. 3b shows the initial deployment of framework 200 wherein the top segments 300 of each of the articulated wire loop 220 are beginning to engage in a circumferential flaring motion and bend out of plane as it is deployed about a plastic mock heart 2. FIG. 3b shows a polymer film 221 with an articulated wire loop 220 with the top segment 300 flanked by the left and right midway bends 320a and 320b and include strut 321a extending from midway bends 320a and strut 321b extending from midway bends 320b as it is deployed from the deployment tube 400. The articulated wire loop 220 is deployed from the deployment tube 400 such that the left and right midway bends 320a and 320b are extending from the deployment tube 400.

Figure 3C:
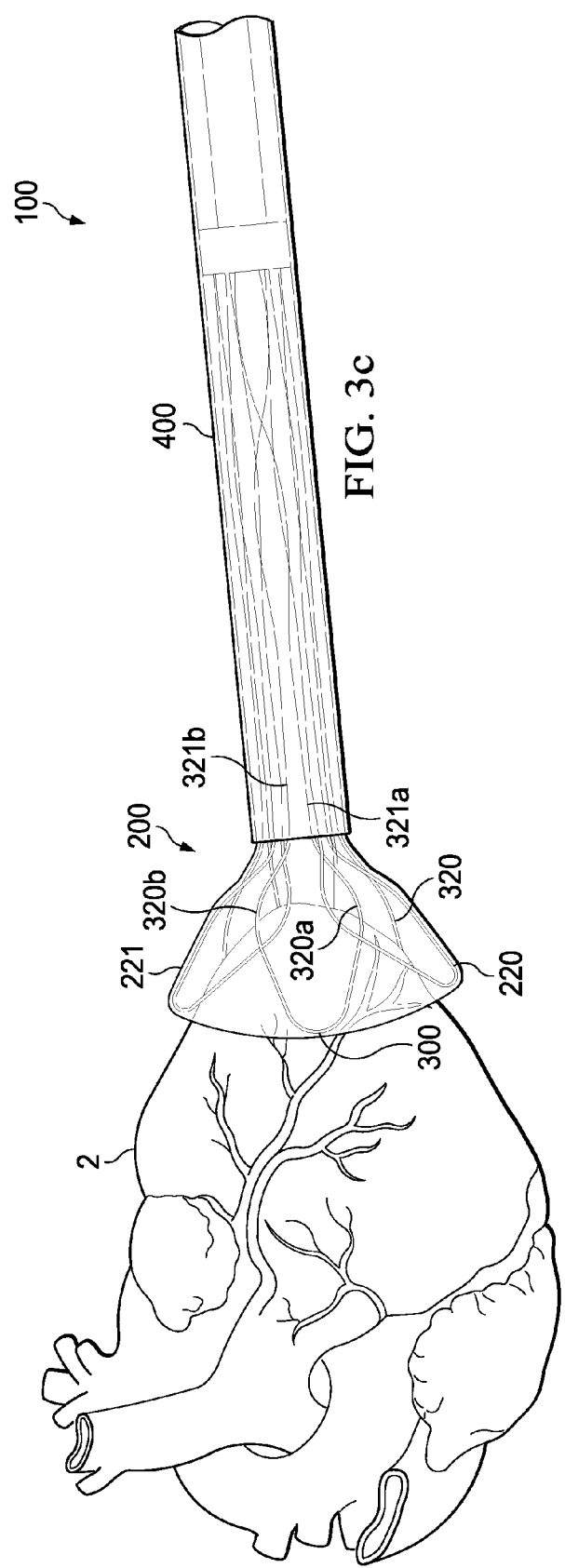

FIG. 3c illustrates the framework deployed to the midway bends 320 which are bent outwards flaring the top segment 300 out. As the framework 200 is deployed pass the midway bends 320, about a plastic mock heart 2. FIG. 3c shows a polymer film 221 with an articulated wire loop 220 with the top segment 300 flanked by the left and right midway bends 320a and 320b and include strut 321a extending from midway bends 320a and strut 321b extending from midway bends 320b as it is deployed from the deployment tube 400. The articulated wire loop 220 is deployed from the deployment tube 400 such that the left and right midway bends 320a and 320b and the polymer film 221 are extending past the deployment tube 400.

FIG. 3d shows the struts 321a and 321b connected to midway bends 320a and 320b which straighten out to configure to a form of higher elastic energy. The framework 200 is deployed pass the midway bends 320, about a plastic mock heart 2. FIG. 3d shows a polymer film 221 with an articulated wire loop 220 with the top segment 300 flanked by the left and right midway bends 320a and 320b and include strut 321a extending from midway bends 320a and strut 321b extending from midway bends 320b as it is deployed from the deployment tube 400. The articulated wire loop 220 is deployed from the deployment tube 400 such that the left and right midway bends 320a and 320b are extending past the deployment tube 400. As the midway bends 320a and 320b are straightened out, the top segment 300 of each articulated wire loop 220 are reoriented inwards from the initial flared position. The reorientation of the articulated wire loops 220 allows the top segment 300 of each wire loop 220 and the polymer film 221 to make contact with the outer circumference of the heart 2.

FIG. 3e illustrates the full deployment of the framework 200 as each articulated wire loop 220 is further expanded to encircle a larger portion of the heart 2. The framework 200 is deployed pass the midway bends 320, about a plastic mock heart 2. FIG. 3e shows a polymer film 221 with an articulated wire loop 220 with the top segment 300 flanked by the left and right midway bends 320a and 320b and include strut 321a extending from midway bends 320a and strut 321b extending from midway bends 320b as it is deployed from the deployment tube 400. The articulated wire loop 220 is deployed from the deployment tube 400 such that the left and right midway bends 320a and 320b and the polymer film 221 are extending past the deployment tube 400 to encircle a larger portion of the heart 2.

The self-expanding wire framework device of the present invention includes multiple articulated wire loops with a polymer film connected thereto. The number of articulated wire loops used is at the discretion of the manufacturer and depends on the size of the deployable device. As little as 2 articulated wire loops can be used, but the number can increase to 3, 4, 5, 6, 7, 8, 9, 10, 11, 12, or more articulated wire loops linked. Each of the articulated wire loops include struts that connect the midway bends to the hub (not shown). The struts are fixed in position relative to the midway bends to induce flaring when extended from the deployment tube. The fixation location can vary with the deployment of the framework as tension between the articulate wire loops may move the linkage. However, the struts between the loops may also be fixated to limit the maximum expansion size of the wire framework.

Figure 4B:
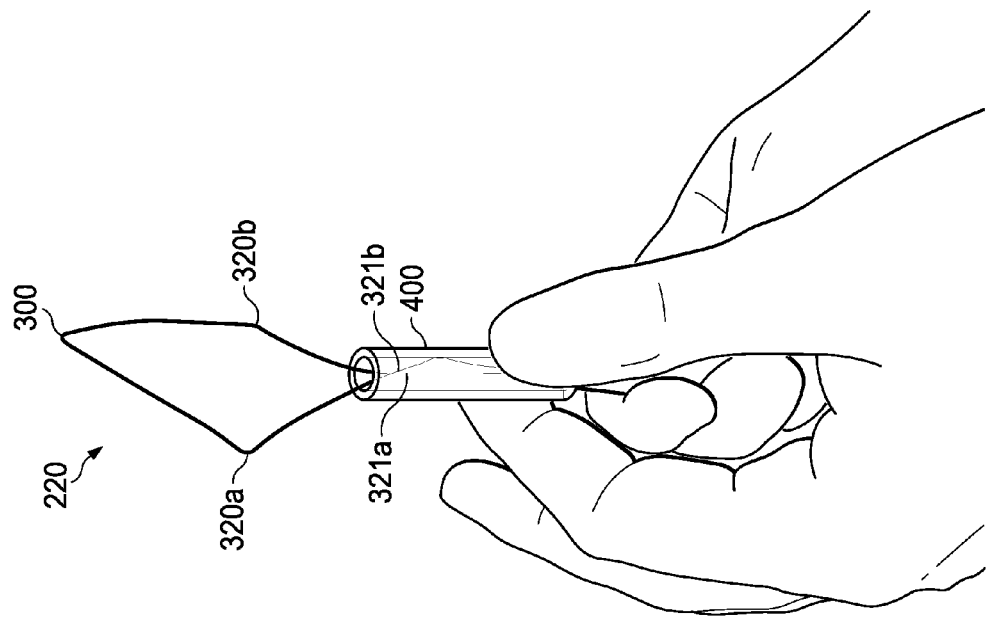
FIGS. 4a-4d depicts a side view of an embodiment of the present invention showing a single articulated wire loop being drawn into the deployment tube.
Figure 4A:
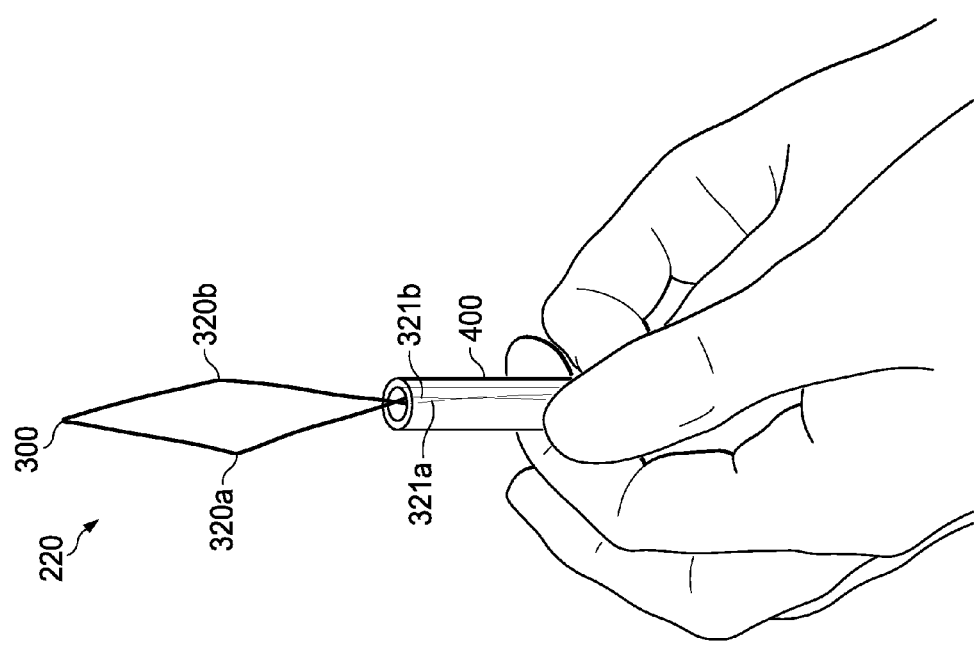
Figure 4D:
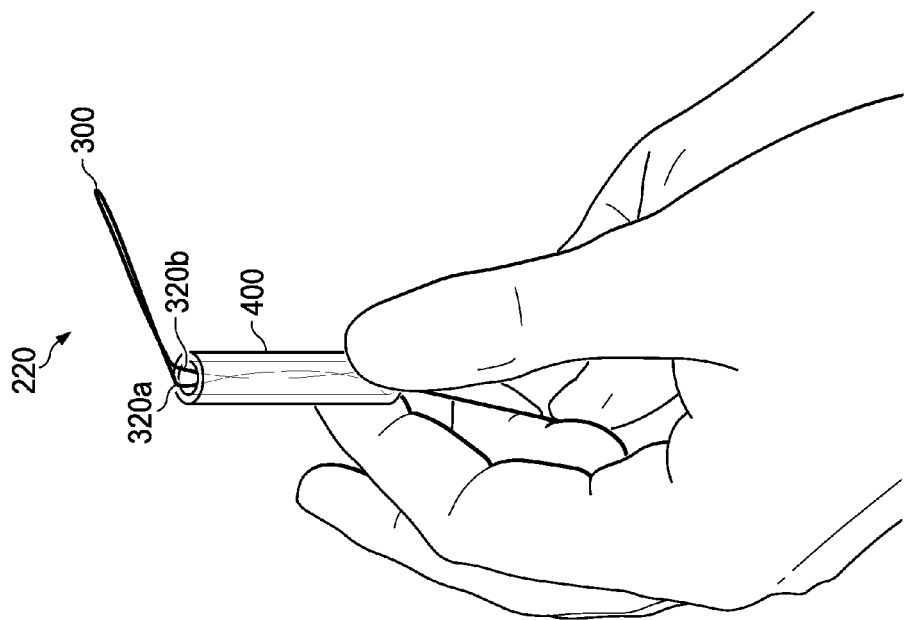
Figure 4C:
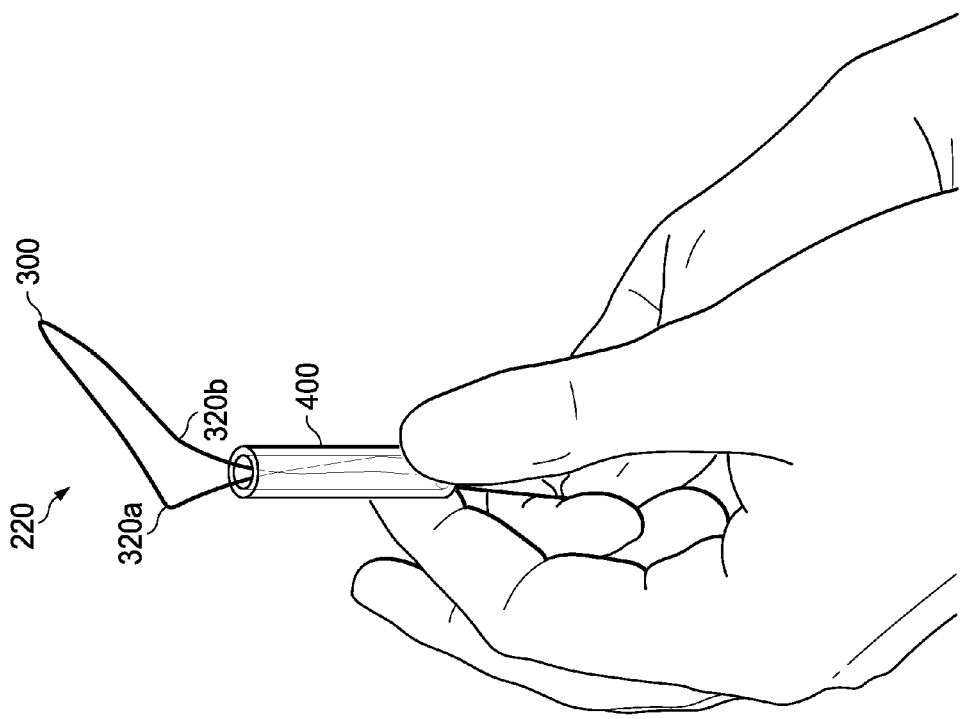

FIGS. 4a-4d depicts a side view of an embodiment of the present invention showing a single articulated wire loop 220 being drawn into the deployment tube 400. In FIG. 4a the articulated loop 220 is beginning to be drawn into the deployment tube 400 which compresses the left and right midway bends 320a and 320b together to allow top segments 300 to move inwardly. In FIG. 4b the articulated loop 220 is beginning to be drawn into the deployment tube 400 which compresses the left and right midway bends 320a and 320b together. At this point, flaring of the top segment 300 is evident between FIGS. 4a and 4b. Instead of the wire loop 220 collapsing in-plane and forced into the deployment tube 400, the left and right midway bends 320a and 320b each rotate to orient their top segments 300 out of plane. FIG. 4c shows an oriented wire loop 220 with the left and right midway bends 320a and 320b bent and flaring the top segment 300 outwardly. FIG. 4d shows the articulated wire loop 220 drawn into the deployment tube 400 to the left and right midway bends 320a and 320b. Each of the articulated wire loops 220 will have a pair of struts extending into the deployment tube 400 that may or may not be compressed. The present invention would still function if the loop ends were crossed or parallel within the deployment tube 400.

Figure 5B:
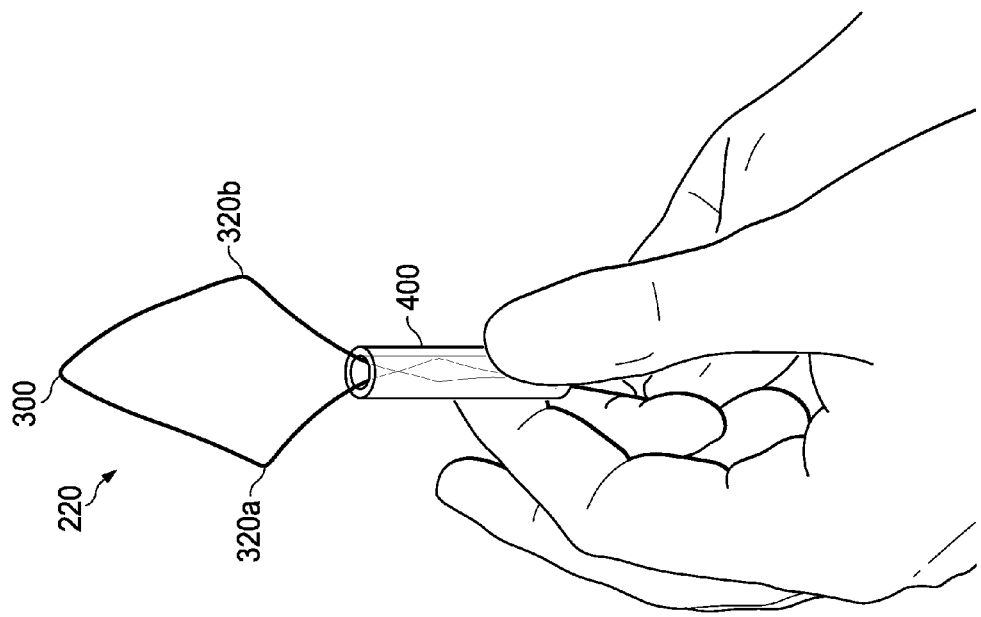
FIGS. 5a-5d depicts a frontal view of an embodiment of the present invention showing a single articulated wire loop being drawn into the deployment tube.
Figure 5A:
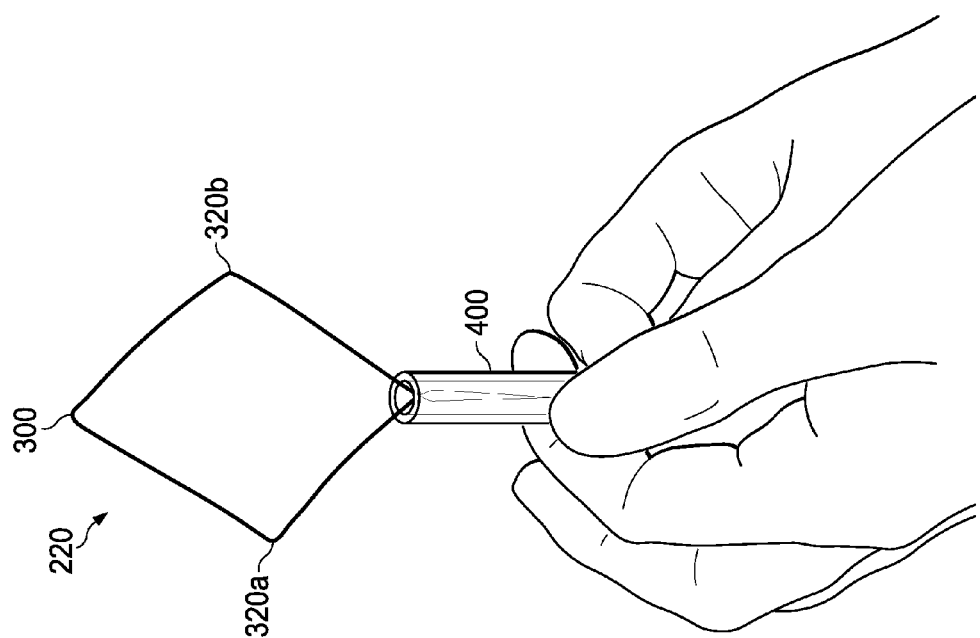
Figure 5D:
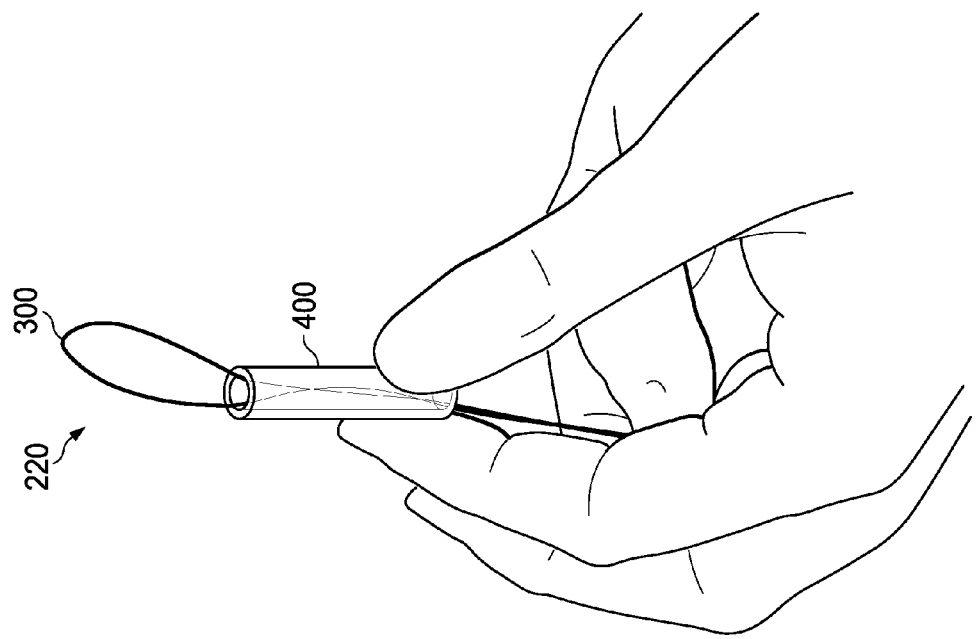
Figure 5C:
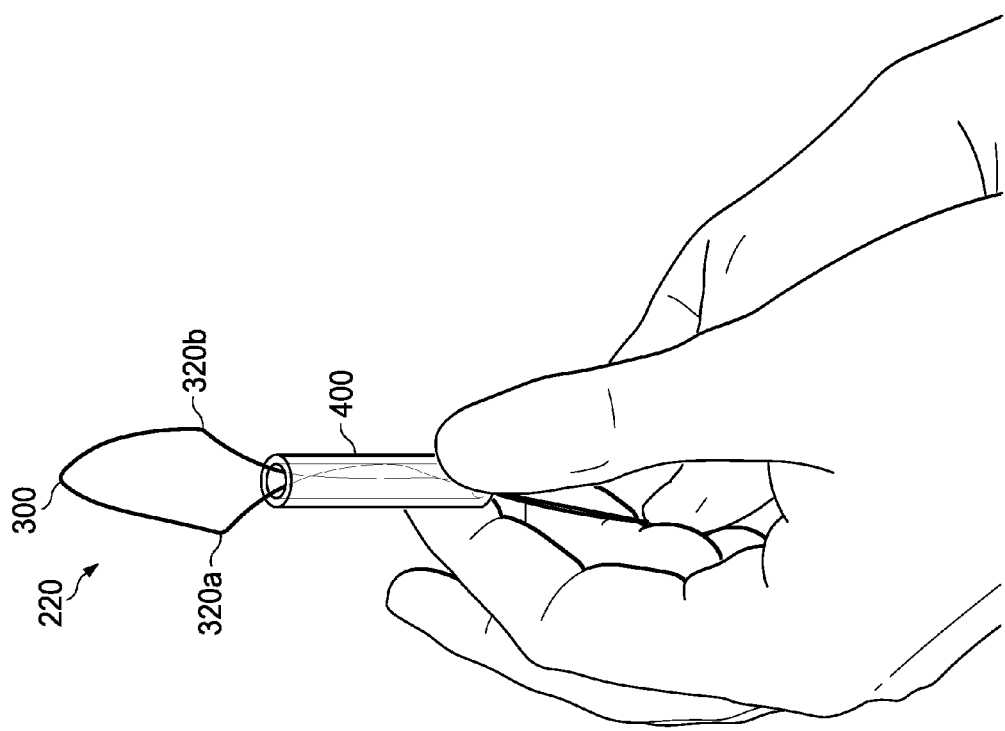

FIGS. 5a-5d depicts a frontal view of the single articulated wire loop 220 being drawn into the deployment tube 400 and correspond with FIGS. 4a-4d respectively. The bending and flaring of the midway bends 320a and 320b in the deployment tube 400 cannot be seen in the frontal view, but the compression of the midway bends 320a and 320b together is clear. FIGS. 5b and 5c show the reorientation of the wire loop 220 as the midway bends 320a and 320b are compressed into the deployment tube 400. FIG. 5d shows that after the midway bends 320a and 320b are reached, the rest of the wire loop up to the top segment 300 are compressed together to be drawn into the deployment tube 400. However, this compressed form is the configuration the loop 220 will be deployed at which leads to the initial flaring out position shown in FIG. 4d when the wire loop 220 is first deployed.

As noted herein, there are a number of features and advantages of the apparatus and method of the present invention, including: the apparatus is adapted to permit deployment of a deployable device, such as a heart assist or cardiac compression device; the self-expanding wire framework equipped with the deployable device being collapsible to fit inside the deployment tube to be positioned near the heart, and then deployed to advance around a heart without the need of any guidewires; the apparatus comprising a minimal number of components—including a self-expanding wire framework adapted to engage a deployable device, expand the deployable device and guide the deployable device during deployment; and the self-expanding wire framework and deployment tube being separated or integrated into a single unit.

Once the self-expanding wire framework is deployed from the deployment, controlled expansion and outward bend of the framework can aid in the positioning and implantation of the deployable device. The wire used for constructing the self-expanding wire frame will need to be an appropriate wire stiffness to achieve desired expansion and flaring out but not cause inversion of the wireframe during deployment. The use of quadrilateral or non-round wires will allow orienting the wire cross section such that it naturally causes the flaring motion upon deployment from the deployment tube. An example would be a rectangular wire with the long length of the cross-section oriented along the periphery of the device, around the heart. Furthermore, when engaging the deployable device with the self-expanding wire framework, the self-expanding wire fragment should be in a flaring position with the top segment 300 of each of the articulated wire loops out of plane.

In other embodiment of the invention, the midway bends of the articulated wire loop can be made more rounded to allow for gradual flaring as the framework is deployed. In another embodiment, the midway bends can also comprise multiple bends (two bends instead of one midway bend). Other embodiments can include 3, 4, 5 or more bends depending on the preference of the manufacturer. The diamond shape of the articulated wire loop is not the only possible element design. Various other shapes and designs are possible as long as there is a bending top segment 300 and midway bends in a left segment and a right segment that bend outward when the wire loop is collapsed and packed into the deployment tube.

Figure 6A:
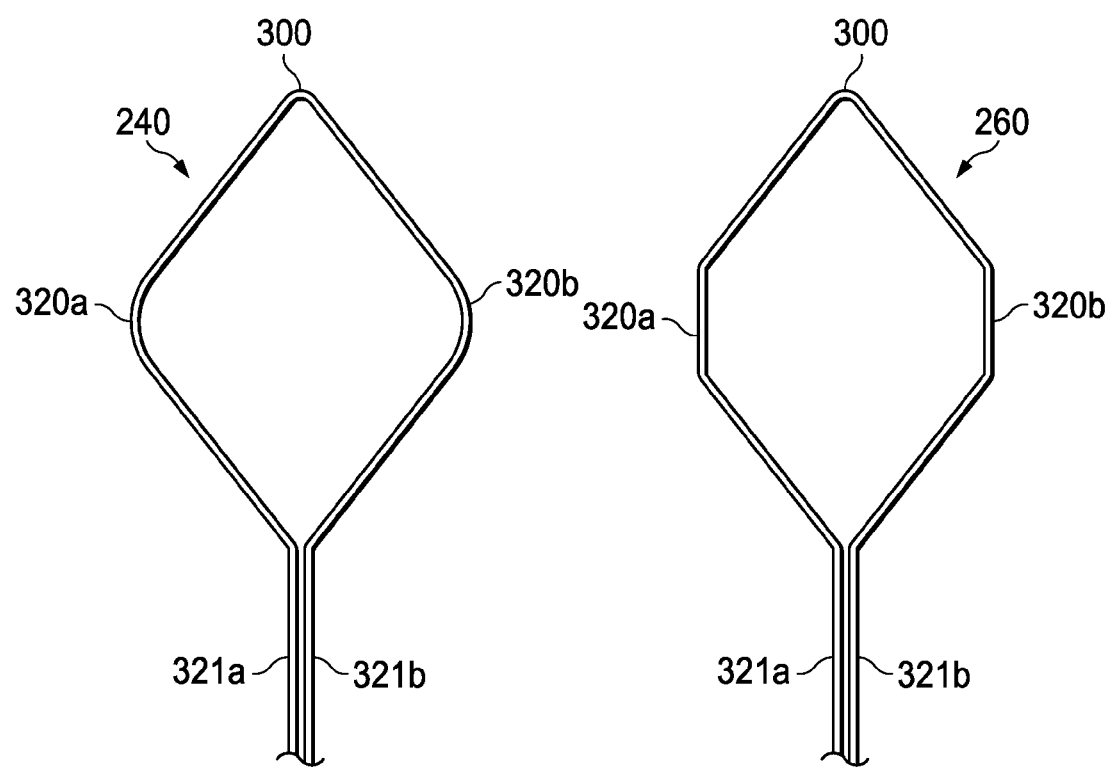
FIGS. 6a-6c depicts other embodiments of the present invention showing different designs of midway bends in the articulate wire loop.

FIG. 6a shows a schematic of an embodiment of articulated wire loop 240 with the top segment 300 flanked by the left and right midway bends 320a and 320b which are more rounded and include strut 321a extending from midway bends 320a and strut 321b extending from midway bends 320b into the deployment tube (not shown). Another embodiment includes articulated wire loop 260 with the top segment 300 flanked by the left and right midway bends 320a and 320b which are more flat and include strut 321a extending from midway bends 320a and strut 321b extending from midway bends 320b into the deployment tube (not shown).

Figure 6C:
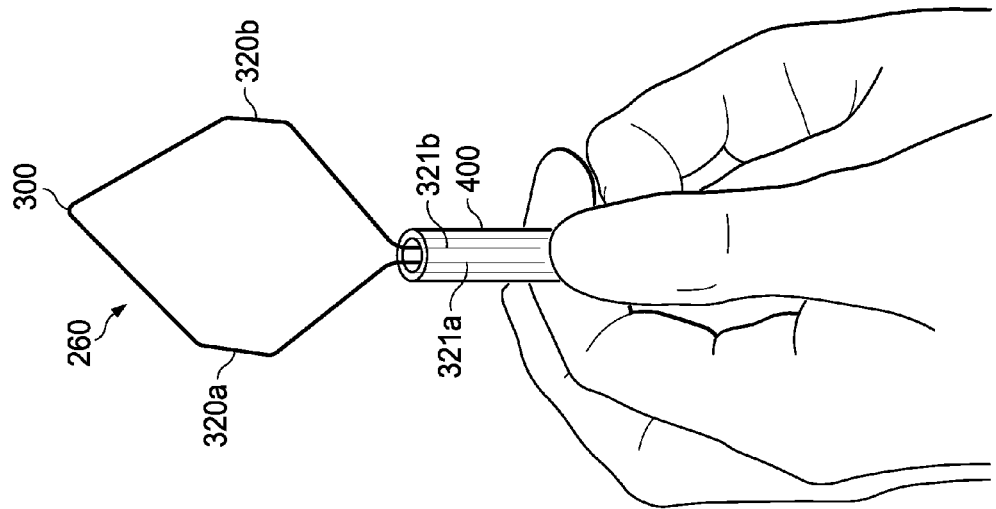
Figure 6B:
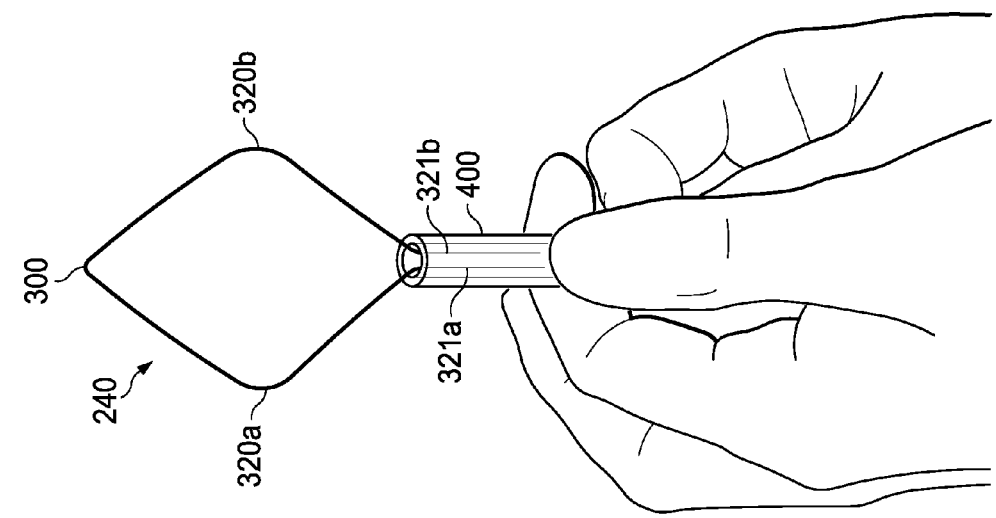

FIG. 6b shows an articulated wire loop 240 with the top segment 300 flanked by the left and right midway bends 320a and 320b which are more rounded and include strut 321a extending from midway bends 320a and strut 321b extending from midway bends 320b into the deployment tube 400.

FIG. 6c shows an articulated wire loop 260 with the top segment 300 flanked by the left and right midway bends 320a and 320b which are more flat and include strut 321a extending from midway bends 320a and strut 321b extending from midway bends 320b into the deployment tube 400.

FIGS. 7a-7d illustrate a side view of articulated wire loop 240 being drawn into deployment tube 400.

Figure 7B:
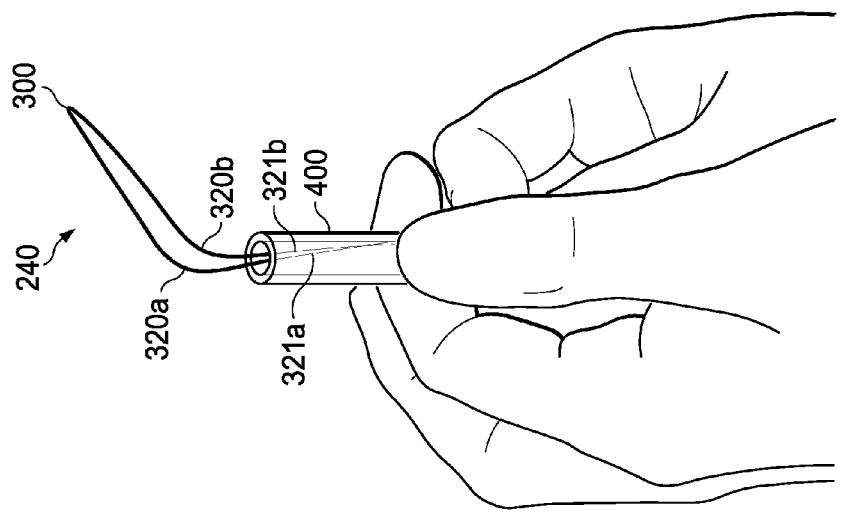
FIGS. 7a-7d depicts a side view of an embodiment of the present invention showing a single articulated wire loop with rounded midway bends being drawn into the deployment tube.
Figure 7A:
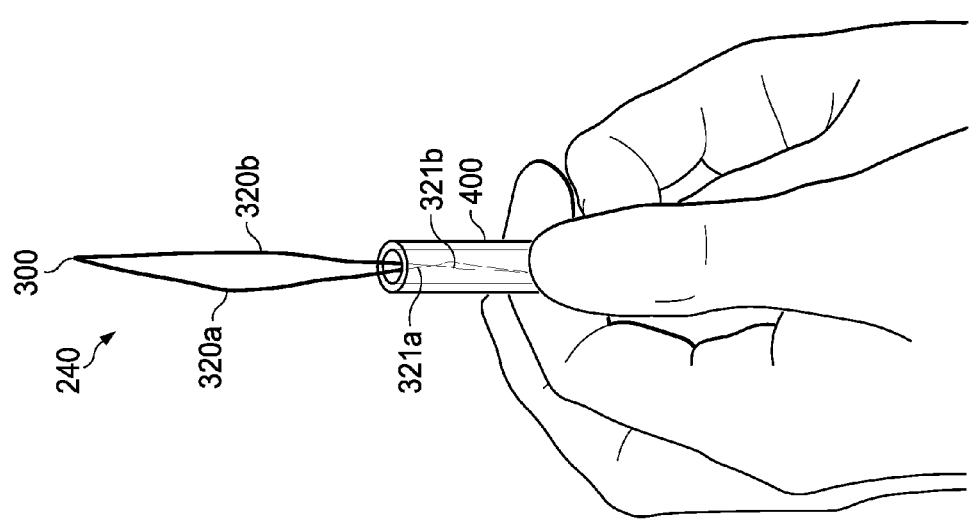

FIG. 7a shows an articulated wire loop 240 with the top segment 300 flanked by the left and right midway bends 320a and 320b which are more rounded and include strut 321a extending from midway bends 320a and strut 321b extending from midway bends 320b drawn into the deployment tube 400.

FIG. 7b shows an articulated wire loop 240 with the top segment 300 flanked by the left and right midway bends 320a and 320b which are more rounded and include strut 321a extending from midway bends 320a and strut 321b extending from midway bends 320b drawn into the deployment tube 400.

Figure 7D:
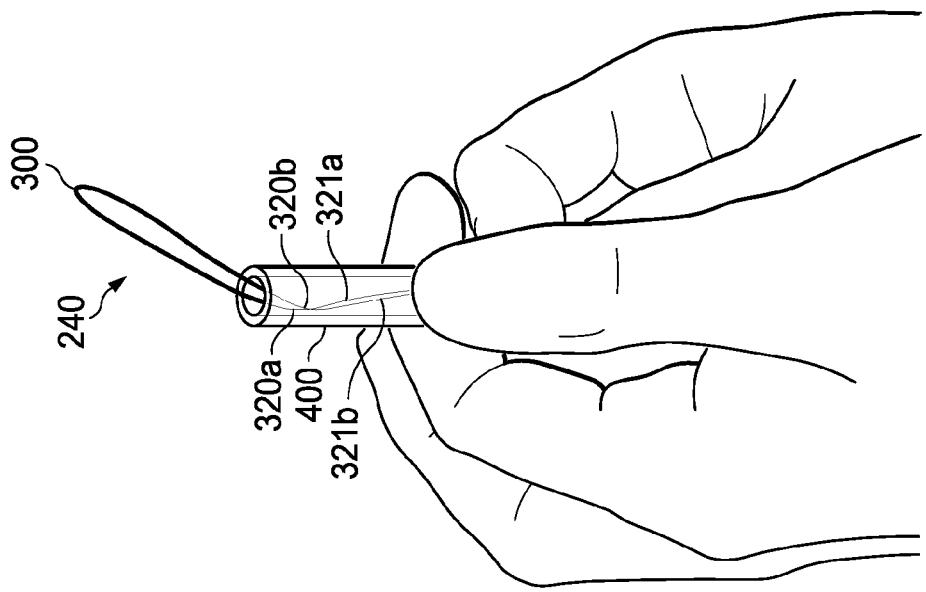
Figure 7C:
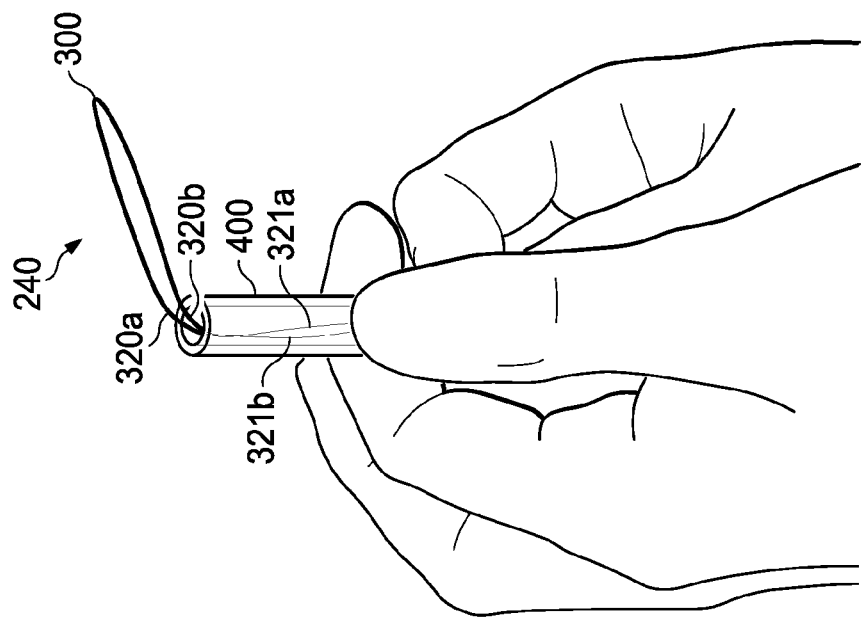

FIG. 7c shows an articulated wire loop 240 with the top segment 300 flanked by the left and right midway bends 320a and 320b which are more rounded and include strut 321a extending from midway bends 320a and strut 321b extending from midway bends 320b drawn into the deployment tube 400. The articulated wire loop 240 is drawn into the deployment tube 400 to the left and right midway bends 320a and 320b.

FIG. 7d shows an articulated wire loop 240 with the top segment 300 flanked by the left and right midway bends 320a and 320b which are more rounded and include strut 321a extending from midway bends 320a and strut 321b extending from midway bends 320b drawn into the deployment tube 400. The articulated wire loop 240 is drawn into the deployment tube 400 such that the left and right midway bends 320a and 320b are within the deployment tube 400.

Figure 8B:
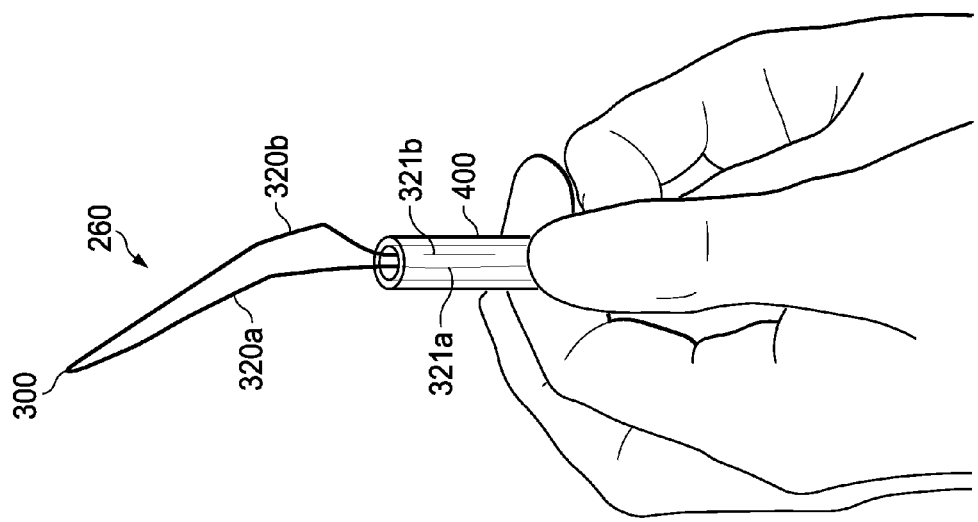
FIGS. 8a-8d depicts a side view of an embodiment of the present invention showing a single articulated wire loop with dual midway bends being drawn into the deployment tube.
Figure 8A:
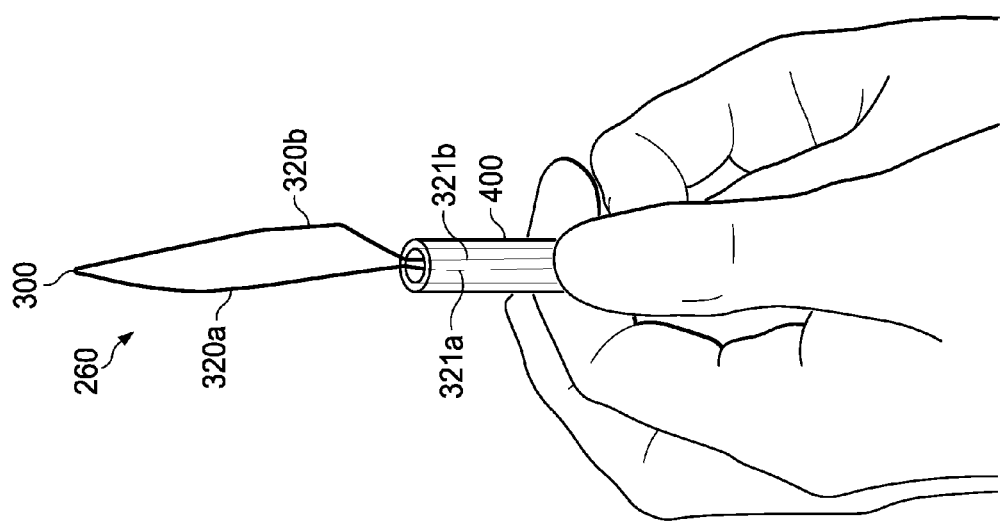

FIG. 8a shows an articulated wire loop 260 with the top segment 300 flanked by the left and right midway bends 320a and 320b which are more rounded and include strut 321a extending from midway bends 320a and strut 321b extending from midway bends 320b drawn into the deployment tube 400.

FIG. 8b shows an articulated wire loop 260 with the top segment 300 flanked by the left and right midway bends 320a and 320b which are more rounded and include strut 321a extending from midway bends 320a and strut 321b extending from midway bends 320b drawn into the deployment tube 400.

Figure 8D:
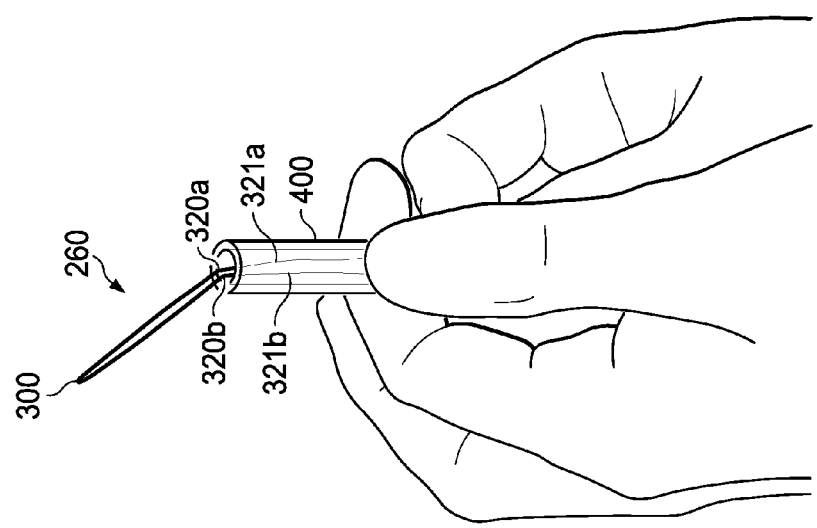
Figure 8C:
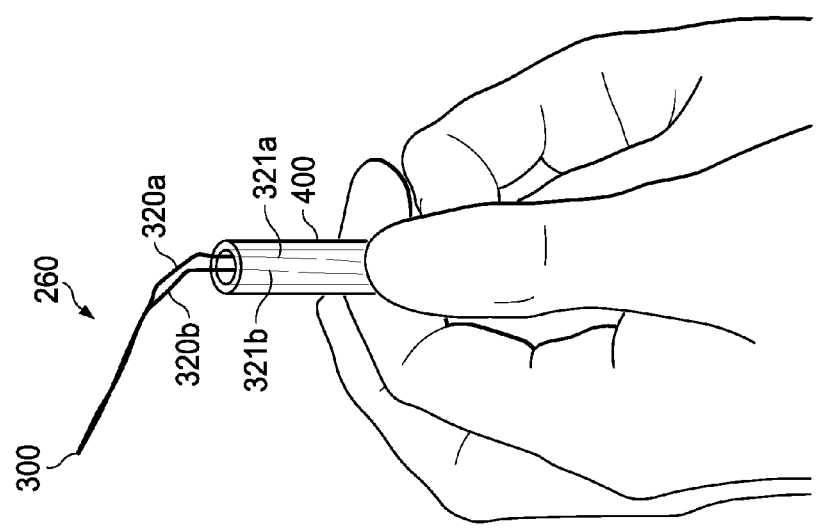

FIG. 8c shows an articulated wire loop 260 with the top segment 300 flanked by the left and right midway bends 320a and 320b which are more rounded and include strut 321a extending from midway bends 320a and strut 321b extending from midway bends 320b drawn into the deployment tube 400. The articulated wire loop 240 is drawn into the deployment tube 400 to the left and right midway bends 320a and 320b.

FIG. 8d shows an articulated wire loop 260 with the top segment 300 flanked by the left and right midway bends 320a and 320b which are more rounded and include strut 321a extending from midway bends 320a and strut 321b extending from midway bends 320b drawn into the deployment tube 400. The articulated wire loop 240 is drawn into the deployment tube 400 such that the left and right midway bends 320a and 320b are within the deployment tube 400.

Various attachment means may also be utilized between a polymer film chamber and the wire frame so as not to impede on desired bending. One example as shown in FIGS. 3a-3e is to strap the wires between layers of plastic. Another embodiment would be to allow wire movement and rotation within the polymer film attachment points.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:
1. A self-expanding wire framework comprising:
a self-expanding wire framework adapted to flare outwardly to encircle a portion of a heart;

a polymer film in contact with the self-expanding wire framework for deployment around the heart, wherein the self-expanding wire framework comprises:
a set of adjacent articulated wire loops extending from a lead edge to a hub, wherein each of the articulated wire loops of the set of articulated wire loops comprise:
a top segment positioned at the lead edge and that extends to a left midway bend and to a right midway bend,
a left strut that extends from the left midway bend to the hub,
a right strut that extends from the right midway bend to the hub, and
a fixed strut attachment point on the hub to fix the position of the left strut and the right strut,
wherein each of the articulated wire loops of the set of articulated wire loops interlace the right strut of a first articulated wire loop with the left strut of an adjacent articulated wire loop, and
wherein the left midway bend and right midway bend result in a tension that causes the set of articulated wire loops to engage in a circumferential flaring motion and bend outwardly as the self-expanding framework is deployed from a deployment tube to outwardly flair the self-expanding wire framework and the polymer film.

2. The device of claim 1, wherein the left midway bends and the right midway bends are rounded to allow for gradual flaring as the self-expanding wire framework is deployed or wherein the left midway bends and the right midway bends are flattened to allow for flaring as the self-expanding wire framework is deployed.

3. The device of claim 1, wherein the left midway bends and the right midway bends further comprise multiple bends to allow for immediate flaring positions as the self-expanding wire framework is deployed.

4. The device of claim 1, wherein the articulated wire loops comprises flat wires, oval wires, round wires, non-rounded wires.

5. The device of claim 1, where the set of articulated wire loops comprises at least 2, 3, 4, 5, 6, 7, 8, 9, 10, 11, 12, 13, 14, 15, 16, 17, 18, 19, 20 or more articulated wire loops.

6. The device of claim 1, wherein the set of articulated wire loops are interlaced by weaving, attaching, looping, welding, bonding or connecting the left strut to an adjacent right strut between the midway bend and the hub.

7. The device of claim 1, wherein the left strut is intertwined with the right strut between the midway bend and the hub.

8. The device of claim 1, wherein the left strut and the right strut are connected separately at the hub.

9. The device of claim 1, wherein each of the articulated wire loops of the set of articulated wire loops is positioned adjacent to an adjacent articulated wire loop.

10. The device of claim 1, wherein each of the articulated wire loops of the set of articulated wire loops is positioned to at least partially overlap the adjacent articulated wire loop.

11. The device of claim 1, wherein the polymer film is on the inside of the self-expanding wire framework, on the outside of the self-expanding wire framework or on the inside and the outside to sandwich the self-expanding wire framework.

12. The device of claim 1, wherein the left strut and the right strut each comprise a bend end connected to the midway bend and a hub end, wherein the hub end is secured to the hub at a fixed strut attachment point.

13. The device of claim 1, wherein the deployment tube having an outer surface surrounding an inner passage and a deployment aperture at one end of the inner passage, wherein the self-expanding wire framework covered with a polymer film is slidably positioned in the inner passage to slidably extend from the deployment aperture and adapted to flare outwardly to encircle a larger portion of the heart.

14. The device of claim 13, wherein the self-expanding wire framework is positioned inside the deployment tube.

15. A self-expanding framework device adapted to facilitate the deployment of an extra-cardiac device, comprising:
a deployment tube having an outer surface surrounding an inner passage and a deployment aperture at one end of the inner passage, and
a self-expanding wire framework adapted to flare outwardly to encircle a portion of a heart and covered with a polymer film and slidably positioned in the inner passage to slidably extend from the deployment aperture, wherein the self-expanding wire framework comprises:
a set of articulated wire loops extending from a lead edge to a hub, wherein each of the articulated wire loops of the set of articulated wire loops comprise:
a top segment positioned at the lead edge and that extends to a left midway bend and to a right midway bend,
a left strut that extends from the left midway bend to the hub,
a right strut that extends from the right midway bend to the hub, and
a fixed strut attachment point on the hub to fix the position of the left strut and the right strut,
wherein each of the articulated wire loops of the set of articulated wire loops interlace the right strut of a first articulated wire loop with the left strut of an adjacent articulated wire loop and the left midway bend and right midway bend result in a tension that causes the self-expanding wire framework and the polymer film to circumferential flair and bend outwardly as the self-expanding framework is deployed from the deployment tube.

16. The device of claim 15, wherein the left midway bends and the right midway bends are rounded to allow for gradual flaring as the self-expanding wire framework is deployed from the deployment tube or the left midway bends and the right midway bends are flattened to allow for flaring as the self-expanding wire framework is deployed from the deployment tube.

17. The device of claim 15, wherein the left midway bends and the right midway bends further comprise multiple bends to allow for immediate flaring positions as the self-expanding wire framework is deployed from the deployment tube.

18. The device of claim 15, where the set of articulated wire loops comprises at least 2, 3, 4, 5, 6, 7, 8, 9, 10, 11, 12, 13, 14, 15, 16, 17, 18, 19, 20 or more articulated wire loops.

19. The device of claim 15, wherein the left strut and the right strut are intertwined or the left strut and the right strut are fixed at the hub.

20. The device of claim 15, wherein each of the articulated wire loops of the set of articulated wire loops is positioned adjacent to an adjacent articulated wire loop.

21. The device of claim 15, wherein each of the articulated wire loops of the set of articulated wire loops is positioned to at least partially overlap the adjacent articulated wire loop.

22. The device of claim 15, wherein the polymer film is on the inside of the self-expanding wire framework, the polymer film is on the outside of the self-expanding wire framework or the polymer film is on the inside and the outside to sandwich the self-expanding wire framework.

23. A method for implanting a self-expanding framework delivery device about a heart, comprising the steps of:

providing a self-expanding framework delivery device comprising a deployment tube having an outer surface surrounding an inner passage and a deployment aperture at one end of the inner passage, and a self-expanding wire framework adapted to flare outwardly to encircle a portion of a heart and covered with a polymer film and slidably positioned in the inner passage to slidably extend from the deployment aperture, wherein the self-expanding wire framework comprises: a set of articulated wire loops extending from a lead edge to a hub, wherein each of the articulated wire loops of the set of articulated wire loops comprise a top segment positioned at the lead edge and that extends to a left midway bend and to a right midway bend, a left strut that extends from the left midway bend to the hub, a right strut that extends from the right midway bend to the hub, and a fixed strut attachment point on the hub to fix the position of the left strut and the right strut, wherein each of the articulated wire loops of the set of articulated wire loops interlace the right strut of a first articulated wire loop with the left strut of an adjacent articulated wire loop and the left midway bend and right midway bend result in a tension that causes the self-expanding wire framework and the polymer film to circumferentially flair and bend outwardly as the self-expanding framework is deployed from the deployment tube;

inserting the deployment tube into the thoracic cavity;

deploying the self-expanding wire framework covered with a polymer film from the deployment aperture;

bending outwardly of the self-expanding framework at the left midway bend and right midway to circumferential flare the lead edge of the articulated wire loops about the apex of the heart; and extending the self-expanding wire framework from the deployment aperture to encircle a portion of the heart.

* * * * *